(12) United States Patent
Smith et al.

(10) Patent No.: US 8,697,088 B2
(45) Date of Patent: Apr. 15, 2014

(54) VLPS DERIVED FROM CELLS THAT DO NOT EXPRESS A VIRAL MATRIX OR CORE PROTEIN

(75) Inventors: Gale Smith, Rockville, MD (US); Peter Pushko, Rockville, MD (US); Kutub Mahmood, Rockville, MD (US); Bin Zhao, Rockville, MD (US)

(73) Assignee: Novavax, Inc., Gaithersburg, MD (US)

( * ) Notice: Subject to any disclaimer, the term of this patent is extended or adjusted under 35 U.S.C. 154(b) by 185 days.

(21) Appl. No.: 12/127,625

(22) Filed: May 27, 2008

(65) Prior Publication Data

US 2009/0017066 A1    Jan. 15, 2009

Related U.S. Application Data

(60) Provisional application No. 60/940,201, filed on May 25, 2007.

(51) Int. Cl.
*A61K 39/145* (2006.01)
*C12N 15/44* (2006.01)

(52) U.S. Cl.
USPC ........................................ 424/209.1; 435/456

(58) Field of Classification Search
USPC ..................................................... 424/209.1
See application file for complete search history.

(56) References Cited

U.S. PATENT DOCUMENTS

| | | |
|---|---|---|
| 2003/0138881 A1 | 7/2003 | Lazetic et al. |
| 2007/0042001 A1 * | 2/2007 | Weeks-Levy et al. ..... 424/209.1 |
| 2007/0042002 A1 * | 2/2007 | Weeks-Levy et al. ..... 424/209.1 |
| 2008/0008725 A1 * | 1/2008 | Weeks-Levy et al. ..... 424/209.1 |

FOREIGN PATENT DOCUMENTS

| | | |
|---|---|---|
| WO | WO 02/00885 | 1/2002 |
| WO | WO 2006/045532 A2 * | 5/2006 |

OTHER PUBLICATIONS

Flandorfer et al. Journal of Virology, Sep. 2003, p. 9116-9123, vol. 77, No. 17.*
Pushuko et al. Vaccine 2005, vol. 23 (50) pp. 5751-5759).*
Latham J. et al. J. Virol. 2001, vol. 75, No. 13, pp. 6154-6165.*
Chen, et al., "Influenza Virus Hemagglutinin and Neuraminidase, but Not the Matrix Protein, Are Required for Assembly and Budding of Plasmid-Derived Virus-Like Particles," *J. Virology* 81(13): 7111-7123 (Jul. 2007), E-Publication May 2, 2007.
Melikyan, et al., "Amino Acid Sequence Requirements of the Transmembrane and Cytoplasmic Domains of Influenza Virus Hemagglutinin for Viable Membrane Fusion," *M. Biol Cell* 10: 1821-1836 (Jun. 1999).
International Search Report and Written Opinion mailed Aug. 15, 2008 in the International (PCT) Application No. PCT/US08/64911.
Szecsi, et al., "Induction of neutralising antibodies by virus-like particles harbouring surface proteins from highly pathogenic H5N1 and H7N1 influenza viruses," *Virology Journal* 3:70 (Sep. 3, 2006).

* cited by examiner

*Primary Examiner* — Bao Li
(74) *Attorney, Agent, or Firm* — Cooley LLP

(57) ABSTRACT

The present invention discloses novel influenza virus-like particles (VLPs) that contain chimeric proteins or influenza membrane proteins. The chimeric proteins are derived from fragments of influenza membrane proteins fused to heterologous proteins. The invention includes antigenic formulations and vaccines comprising VLPs of the invention as well as methods of making and administering VLPs to vertebrates, including methods of inducing immunity to infections, such as influenza.

20 Claims, 10 Drawing Sheets

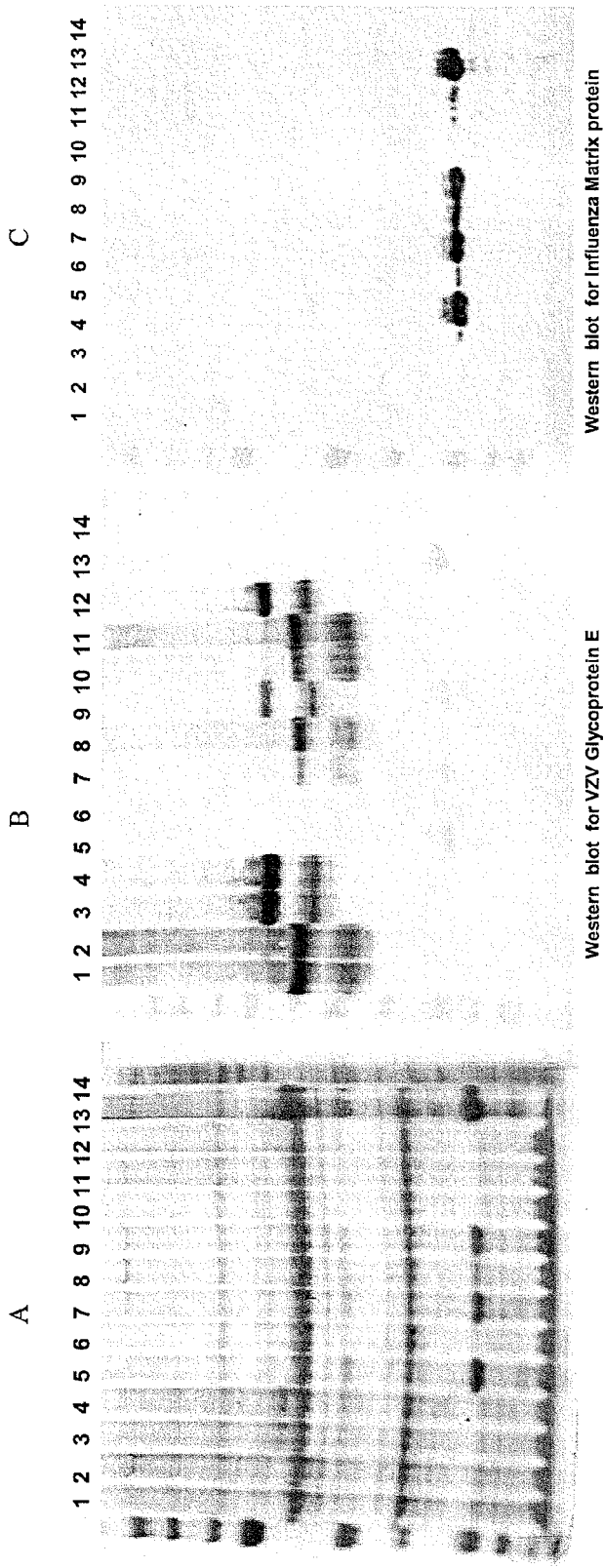

SEQUENCE LISTING

```
<160> NUMBER OF SEQ ID NOS: 6

<210> SEQ ID NO 1
<211> LENGTH: 36
<212> TYPE: PRT
<213> ORGANISM: Influenza virus

<400> SEQUENCE: 1

Leu Ser Ile Tyr Ser Thr Val Ala Ser Ser Leu Ala Leu Ala Ile Met
1               5                   10                  15

Met Ala Gly Leu Ser Leu Trp Met Cys Ser Asn Gly Ser Leu Gln Cys
            20                  25                  30

Arg Ile Cys Ile
        35

<210> SEQ ID NO 2
<211> LENGTH: 73
<212> TYPE: PRT
<213> ORGANISM: Influenza virus

<400> SEQUENCE: 2

Pro Leu Thr Ile Ala Ala Asn Ile Ile Gly Ile Leu His Leu Thr Leu
1               5                   10                  15

Trp Ile Leu Asp Arg Leu Phe Phe Lys Cys Ile Tyr Arg Arg Phe Lys
            20                  25                  30

Tyr Gly Leu Lys Gly Gly Pro Ser Thr Glu Gly Val Pro Lys Ser Met
        35                  40                  45

Arg Glu Glu Tyr Arg Lys Glu Gln Gln Ser Ala Val Asp Ala Asp Asp
    50                  55                  60

Gly His Phe Val Ser Ile Glu Leu Glu
65                  70

<210> SEQ ID NO 3
<211> LENGTH: 29
<212> TYPE: PRT
<213> ORGANISM: Influenza virus

<400> SEQUENCE: 3

Ile Ile Thr Ile Gly Ser Ile Cys Met Val Ile Gly Ile Val Ser Leu
1               5                   10                  15

Met Leu Gln Ile Gly Asn Met Met Asn Pro Asn Gln Lys
            20                  25

<210> SEQ ID NO 4
<211> LENGTH: 575
<212> TYPE: PRT
<213> ORGANISM: Artificial Sequence
<220> FEATURE:
<223> OTHER INFORMATION: VZV gE-HA transmembrane chimeric protein

<400> SEQUENCE: 4

Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
            20                  25                  30
```

```
Leu Arg Tyr Asp Asp Phe His Thr Asp Glu Asp Lys Leu Asp Thr Asn
        35                  40                  45

Ser Val Tyr Glu Pro Tyr Tyr His Ser Asp His Ala Glu Ser Ser Trp
50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
                100                 105                 110

Arg Leu Met Gln Pro Thr Gln Met Ser Ala Gln Glu Asp Leu Gly Asp
            115                 120                 125

Asp Thr Gly Ile His Val Ile Pro Thr Leu Asn Gly Asp Asp Arg His
        130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
                180                 185                 190

Gly Val Arg Tyr Thr Glu Thr Trp Ser Phe Leu Pro Ser Leu Thr Cys
            195                 200                 205

Thr Gly Asp Ala Ala Pro Ala Ile Gln His Ile Cys Leu Lys His Thr
        210                 215                 220

Thr Cys Phe Gln Asp Val Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
                260                 265                 270

Glu Leu Glu Leu Asp Pro Pro Glu Ile Glu Pro Gly Val Leu Lys Val
            275                 280                 285

Leu Arg Thr Glu Lys Gln Tyr Leu Gly Val Tyr Ile Trp Asn Met Arg
        290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
                340                 345                 350

Val Gly Asp Thr Phe Ser Leu Ala Met His Leu Gln Tyr Lys Ile His
            355                 360                 365

Glu Ala Pro Phe Asp Leu Leu Leu Glu Trp Leu Tyr Val Pro Ile Asp
        370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
        435                 440                 445
```

-continued

```
Glu Pro Ser Phe Gly Leu Ile Leu His Asp Gly Thr Thr Leu Lys
    450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
                485                 490                 495

Val Asp His Phe Val Asn Ala Ile Glu Glu Arg Gly Phe Pro Pro Thr
                500                 505                 510

Ala Gly Gln Pro Pro Ala Thr Thr Lys Pro Lys Glu Ile Thr Pro Val
            515                 520                 525

Asn Pro Gly Thr Ser Pro Leu Leu Arg Gln Ile Leu Ser Ile Tyr Ser
        530                 535                 540

Thr Val Ala Ser Ser Leu Ala Leu Ala Ile Met Met Ala Gly Leu Ser
545                 550                 555                 560

Leu Trp Met Cys Ser Asn Gly Ser Leu Gln Cys Arg Ile Cys Ile
                565                 570                 575

<210> SEQ ID NO 5
<211> LENGTH: 5
<212> TYPE: PRT
<213> ORGANISM: Influenza virus

<400> SEQUENCE: 5

Arg Arg Arg Lys Arg
1               5

<210> SEQ ID NO 6
<211> LENGTH: 4
<212> TYPE: PRT
<213> ORGANISM: Artificial Sequence
<220> FEATURE:
<223> OTHER INFORMATION: Mutated cleavage site sequence

<400> SEQUENCE: 6

Arg Glu Ser Arg
1
```

VLPS DERIVED FROM CELLS THAT DO NOT EXPRESS A VIRAL MATRIX OR CORE PROTEIN

CROSS-REFERENCE TO RELATED APPLICATIONS

This application claims priority to U.S. provisional application 60/940,201, filed May 25, 2007, which is herein incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing of the Sequence Listing (filename: NOVV_017_01US_SeqList_ST25.txt, date recorded: May 27, 2008, file size 7 kilobytes).

BACKGROUND

Influenza virus is a member of the Orthomyxoviridae family, and can be further classified into three subtypes: A, B, and C (for review, see Murphy and Webster, (1996) Virology, Vol. 1, pp. 1397-1444. Lippincott-Raven, Philadelphia). Influenza subtype A causes the most severe disease in humans. The A strain can be subdivided into different serotypes according to which forms of two surface antigens (hemagglutinin and neuraminidase) are expressed. The influenza virus is an enveloped, segmented, negative strand RNA virus, which encodes several viral proteins. The mature influenza virion contains hemagglutinin (HA), neuraminidase (NA), matrix (M1), proton ion-channel protein (M2), nucleoprotein (NP), polymerase basic protein 1 (PB1), polymerase basic protein 2 (PB2), polymerase acidic protein (PA), and nonstructural protein 2 (NS2) proteins. The HA, NA, M1, and M2 are membrane associated, whereas NP, PB1, PB2, PA, and NS2 are nucleocapsid associated proteins. The NS1 is the only nonstructural protein not associated with virion particles but specific for influenza-infected cells. The M1 protein is the most abundant protein in influenza particles. The HA and NA proteins are envelope glycoproteins, responsible for virus attachment and penetration of the viral particles into the cell, and the sources of the major immunodominant epitopes for virus neutralization and protective immunity. Both HA and NA proteins are considered the most important components for prophylactic influenza vaccines.

Influenza virus infection is initiated by the attachment of the virion surface HA protein to a sialic acid-containing cellular receptor (glycoproteins and glycolipids). The NA protein mediates processing of the sialic acid receptor, and virus penetration into the cell occurs through a receptor-mediated endocytosis, which is dependent on the viral HA protein. Within the acidic endosomes, the HA proteins of internalized influenza virions undergo conformational changes that lead to fusion of viral and host cell membranes followed by virus uncoating, and M2-mediated release of M1 proteins from nucleocapsid-associated ribonucleoproteins (RNPs). The RNPs then migrate into the cell nucleus for viral RNA synthesis. Antibodies to HA molecules can prevent virus infection by neutralizing virus infectivity, whereas antibodies to NA proteins mediate their effect on the early steps of viral replication.

Inactivated influenza A and B virus vaccines are currently sold as trivalent vaccines for parenteral administration. These trivalent vaccines are produced as monovalent bulk in the allantoic cavity of embryonated chick eggs, purified by rate zonal centrifugation or column chromatography, inactivated with formalin or β-propiolactone, and formulated as a blend of the type A and type B strains of influenza viruses in circulation among the human population for a given year. The available commercial influenza vaccines are whole virus (WV) or subvirion (SV; split or purified surface antigen) virus vaccines. The WV vaccine contains intact, inactivated virions. SV vaccines treated with solvents such as tri-n-butyl phosphate (Flu-Shield, Wyeth-Lederle) contain nearly all of the viral structural proteins and some of the viral envelope proteins. SV vaccines solubilized with Triton X-100 (Fluzone, Sanofi-Aventis; Fluvirin, Novartis) contain aggregates of HA monomers, NA, and NP principally, although residual amounts of other viral structural proteins are present. A live attenuated cold-adapted virus vaccine (FluMist, MedImmune) was granted marketing approval by the FDA for commercial usage as an intranasally delivered vaccine indicated for active immunization and the prevention of disease caused by influenza A and B viruses in healthy children and adolescents (5-17 years of age) and healthy adults (18-49 years of age).

Several recombinant products have been developed as recombinant influenza vaccine candidates. These approaches have focused on the expression, production, and purification of influenza virus type A HA and NA proteins, including expression of these proteins using baculovirus infected insect cells (Crawford et al, 1999; Johansson, 1999; Treanor et al., 1996), viral vectors (Pushko et al. (1997), Virology, 239, 389-401; Berglund et al. (1999), Vaccine, 17, 497-507), and DNA vaccine constructs (Olsen et al. (1997), Vaccine, 15, 1149-1156).

Crawford et al. (1999), Vaccine, 17, 2265-2274 demonstrated that influenza HA expressed in baculovirus infected insect cells is capable of preventing lethal influenza disease caused by avian H5 and H7 influenza subtypes. At the same time, another group demonstrated that baculovirus-expressed influenza HA and NA proteins induce immune responses in animals superior to those induced by a conventional vaccine (Johansson et al., (1999) Vaccine, 17, 2073-2080). Immunogenicity and efficacy of baculovirus-expressed hemagglutinin of equine influenza virus was compared to a homologous DNA vaccine candidate (Olsen et al. (1997), Vaccine, 15, 1149-1156). Taken together, these studies demonstrated that a high degree of protection against influenza virus challenge can be induced with recombinant HA or NA proteins, using various experimental approaches and in different animal models.

Lakey et al. (1996), J. Infect Dis., 174, 838-841 showed that a baculovirus-derived influenza HA vaccine was well-tolerated and immunogenic in human volunteers in a Phase I dose escalation safety study. However, results from Phase II studies conducted at several clinical sites in human volunteers vaccinated with several doses of influenza vaccines comprised of HA and/or NA proteins indicated that the recombinant subunit protein vaccines did not elicit protective immunity. These results indicated that conformational epitopes displayed on the surface of HA and NA peplomers of infectious virions were important in the elicitation of neutralizing antibodies and protective immunity.

Regarding the inclusion of other influenza proteins in recombinant influenza vaccine candidates, a number of studies have been carried out, including the experiments involving influenza nucleoprotein, NP, alone or in combination with M1 protein (Ulmer et al. (1993), Science 259, 1745-1749; Ulmer et al. (1998), J. Virol., 72, 5648-5653; Zhou et al. (1995) Proc.

Natl. Acad. Sci., 92, 3009-3013; Tsui et al. (1998), J. Virol., 72, 6907-6910). These vaccine candidates, which were composed of quasi-invariant inner virion proteins, elicited a broad spectrum immunity that was primarily cellular (both CD4+ and CD8+ memory T cells). These experiments involved the use of the DNA or viral genetic vectors. Relatively large amounts of injected DNA were needed, as results from experiments with lower doses of DNA indicated little or no protection (Chen et al., 1998). Hence, further preclinical and clinical research may be required to evaluate whether such DNA-based approaches involving influenza NP and M1 are safe, effective, and persistent.

Recently, in an attempt to develop more effective vaccines for influenza, particulate proteins were used as carriers of influenza M2 protein epitopes. The rationale for development of an M2-based vaccine was that protective immunity against influenza was elicited by M2 proteins in animal studies (Slepushkin et al. (1995), Vaccine, 13, 1399-1402. Neirynck et al. (1999) used a 23-aa long M2 transmembrane domain as an amino terminal fusion partner with the hepatitis B virus core antigen (HBcAg) to expose the M2 epitope(s) on the surface of HBcAg capsid-like particles. However, in spite of the fact that both full-length M2 protein and M2-HBcAg particles induced detectable antibodies and protection in mice, it was unlikely that future influenza vaccines would be based exclusively on the M2 protein, as the M2 protein was present at low copy number per virion, was weakly antigenic, was unable to elicit antibodies that bound free influenza virions, and was unable to block virus attachment to cell receptors (i.e. virus neutralization).

Since previous research has shown that the surface influenza glycoproteins, HA and NA, are the primary targets for elicitation of protective immunity against influenza virus, a new vaccine candidate may include these viral antigens as a protein macromolecular particle, such as a virus-like particle (VLP). VLPs are structurally similar to mature virions, but lack the viral genome making it impossible for viral replication to occur. VLPs can contain antigenic proteins, such as HA, and NA, like intact virus and can be constructed to express foreign structural proteins on their surface as well. Furthermore, the particle with these influenza antigens may display conformational epitopes that elicit neutralizing antibodies to multiple strains of influenza viruses.

Several studies have demonstrated that recombinant influenza proteins could self-assemble into VLPs in cell culture using mammalian expression plasmids or baculovirus vectors (Gomez-Puertas et al. (1999), J. Gen. Virol, 80, 1635-1645; Neumann et al. (2000), J. Virol., 74, 547-551; Latham and Galarza (2001), J. Virol., 75, 6154-6165). Gomez-Puertas et al. (1999), J. Gen. Virol., 80, 1635-1645, demonstrated that efficient formation of influenza VLPs depends on the expression levels of viral proteins. Neumann et al. (2000) established a mammalian expression plasmid-based system for generating infectious influenza virus-like particles entirely from cloned cDNAs. Latham and Galarza (2001) reported the formation of influenza VLPs in insect cells infected with recombinant baculovirus co-expressing HA, NA, M1, and M2 genes. This study demonstrated that influenza virion proteins self-assemble upon co-expression in eukaryotic cells and that the M1 matrix protein was required for VLP production.

SUMMARY OF THE INVENTION

The present invention discloses novel VLPs generated by expressing influenza membrane proteins or chimeras of influenza membrane proteins without the co-expression of influenza M1 matrix protein in eukaryotic host cells. The chimeric proteins are made by fusing either cytoplasmic or transmembrane domains from influenza membrane proteins with antigenic proteins from other influenza subtypes or other infectious agents in cells. The VLPs of the invention find use as antigenic formulations or vaccine preparations.

The present invention provides a purified VLP comprising at least one chimeric influenza membrane protein, wherein the VLP does not contain an influenza matrix (M1) protein. In one embodiment, said VLP further comprises at least one additional protein from an infectious agent. The chimeric protein can contain the cytoplasmic tail or the transmembrane domain from an influenza membrane protein. The influenza membrane protein may be HA, NA, or M2. In another embodiment of the invention, said VLP does not contain a viral matrix or core protein. In another embodiment, said VLP comprises an enzymatically active influenza NA protein.

The present invention also provides a purified VLP comprising at least one influenza membrane protein, wherein the VLP does not contain an influenza matrix (M1) protein. In one embodiment, said VLP further comprises at least one additional protein from an infectious agent. In another embodiment, said influenza membrane protein is HA. The HA protein may be derived from a seasonal or avian HA protein. In another embodiment, said VLP further comprises an influenza NA protein. In another embodiment, said HA and NA are H5N1. In another embodiment, said VLP does not contain a viral matrix or core protein.

The present invention also discloses methods of making VLPs comprising expressing at least one chimeric influenza membrane protein or influenza membrane protein in a cell, and purifying the VLPs, wherein said cell does not express and influenza matrix (M1) protein. In one embodiment, said method further comprises expressing at least one additional protein from an infectious agent in the cell.

The present invention also provides vaccines and antigenic formulations comprising VLPs disclosed herein, including for instance, a VLP comprising at least one chimeric influenza membrane protein, wherein said VLP does not contain an influenza matrix (M1) protein. In some embodiments, vaccines and antigenic formulations comprise a VLP comprising at least one influenza membrane protein, wherein said VLP does not contain an influenza matrix (M1) protein. In other embodiments, said VLP further comprises at least one additional protein from an infectious agent. The invention also discloses methods of inducing protective immunity to an infection in a subject comprising administering a vaccine or antigenic formulation disclosed herein.

Figure 1:
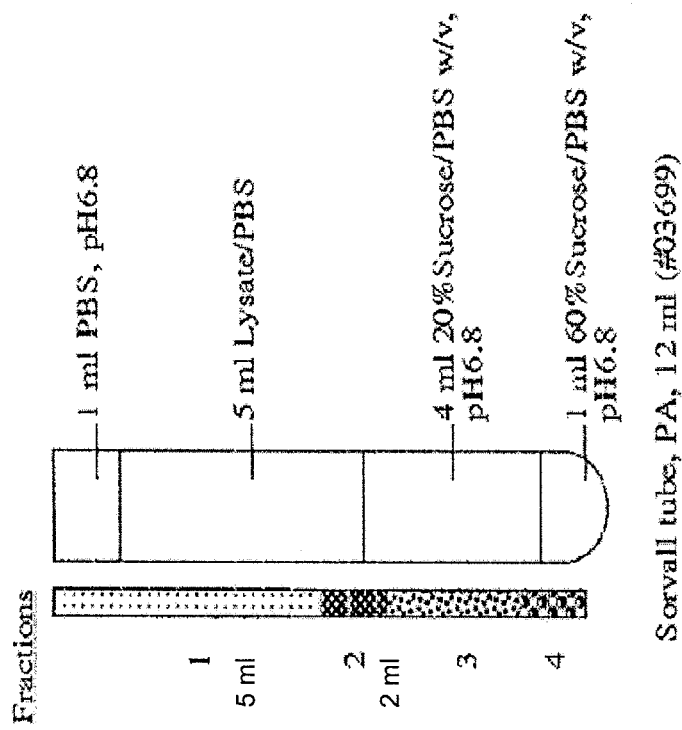
FIG. 1 is a schematic of a sucrose gradient used for the separation of VLPs from contaminants. Fraction numbers are indicated on the left side.

As used herein, the term "antigenic formulation" or "antigenic composition" refers to a preparation which, when administered to a vertebrate, especially a bird or a mammal, will induce a detectable immune response.

As used herein, the term "effective amount" refers to an amount of VLPs necessary or sufficient to realize a desired biologic effect. An effective amount of the composition would be the amount that achieves a selected result, and such an amount could be determined as a matter of routine by a person skilled in the art. For example, an effective amount for preventing, treating and/or ameliorating an infection could be that amount necessary to cause activation of the immune system, resulting in the development of an antigen specific immune response upon exposure to VLPs of the invention. The term is also synonymous with "sufficient amount."

As used herein the term "adjuvant" refers to a compound that, when used in combination with a specific immunogen (e.g. a VLP) in a formulation, augments or otherwise alters or modifies the resultant immune response. Modification of the immune response includes intensification or broadening the specificity of either or both antibody and cellular immune responses. Modification of the immune response can also mean decreasing or suppressing certain antigen-specific immune responses.

As used herein the term "immune stimulator" refers to a compound that enhances an immune response via the body's own chemical messengers (cytokines). These molecules comprise various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc. The immune stimulator molecules can be administered in the same formulation as the influenza VLPs, or can be administered separately. Either the protein or an expression vector encoding the protein can be administered to produce an immunostimulatory effect.

As used herein the term "substantial immunity" refers to an immune response in which administration of VLPs of the invention to a vertebrate induces the immune system in said vertebrate which results in the prevention of infection (e.g. influenza infection), amelioration of infection, or reduction of at least one symptom related to the infection in said vertebrate.

As used herein, the term "protective immunity" or "protective immune response" refers to immunity or eliciting an immune response against an infectious agent, which is exhibited by a vertebrate (e.g., a human), that prevents or ameliorates an infection or reduces at least one symptom thereof.

As use herein, the term "vertebrate" or "subject" or "patient" refers to any member of the subphylum cordata, including, without limitation, humans and other primates, including non-human primates such as chimpanzees and other apes and monkey species. Farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like are also non-limiting examples. The terms "mammals" and "animals" are included in this definition. Both adult and newborn individuals are intended to be covered.

Influenza remains a pervasive public health concern despite the availability of specific inactivated virus vaccines that are 60-80% effective under optimal conditions. When these vaccines are effective, illness is usually averted by preventing viral infection. The lack of effective influenza vaccine programs is partially due to the relatively short persistence of immunity elicited by the current vaccines. Restricted use of these vaccines because of vaccine reactogenicity and side effects in young children, elderly, and people with allergies to components of eggs, which are used in manufacturing of commercially licensed inactivated virus influenza vaccines, also contributes to the persistence of infection with influenza virus.

Vaccine failure can occur as a result of accumulated antigenic differences (antigenic shift and antigenic drift), in the HA and NA proteins leading to the emergence of different viral strains. For example, avian influenza virus type A H9N2 co-circulated with human influenza virus type A Sydney/97 (H3N2) in pigs and led to genetic reassortment and emergence of new strains of human influenza virus with pandemic potential (Peiris et al., 2001). In the event of such antigenic shift, it is unlikely that current vaccines would provide adequate protection.

Additionally, inactivated influenza virus vaccines often lack proper HA and NA conformational epitopes, which elicit neutralizing antibodies and play a major role in protection against disease. Thus, inactivated viral vaccines, as well as some recombinant monomeric influenza subunit protein vaccines, deliver inadequate protection. On the other hand, macromolecular protein structures, such as capsomers, subviral particles, and/or VLPs, include multiple copies of native proteins exhibiting conformational epitopes, which are advantageous for optimal vaccine immunogenicity.

VLPs of the Invention and Methods of Making VLPs

The inventors have discovered that expressing an influenza membrane protein, such as M2, HA, or NA, in the absence of influenza matrix M1 protein leads to the formation of VLPs. Alternatively, expression of chimeric influenza proteins that comprise influenza cytoplasmic and/or transmembrane domains in the absence of M1 matrix protein can also lead to VLP formation. Chimeric proteins can be constructed from either the transmembrane domain or cytoplasmic tails of Orthomyxovirusmembrane proteins, e.g. influenza, fused to extracellular domains from antigenic proteins derived from other viral strains or other infectious agents. Thus, VLPs of the invention are useful for preparing vaccines against infectious agents as well as influenza viruses.

One advantageous feature of the invention is the ability to replace the surface glycoproteins with different subtypes of HA, NA, and/or antigenic proteins from other infectious agents expressed in the VLPs. There are 16 different HA proteins and 9 different NA proteins, all of which have been found among wild birds. Wild birds are the primary natural reservoir for all types of influenza A viruses and are thought to be the source of all types of influenza A viruses in all other vertebrates. Subtypes of influenza viruses are classified by changes in the HA and NA proteins on their surface. Many different combinations of HA and NA proteins are possible. Each combination represents a different type of influenza A virus. In addition, each type can be further classified into strains based on different mutations found in each of its 8 genes. As antigenic variants of HA and NA are identified, the VLPs can be updated to include these new variants (e.g. for seasonal influenza vaccines). In addition, surface glycoproteins from potentially pandemic viruses, such as H5N1, or other HA, NA combinations with pandemic potential could be incorporated into VLPs without concern of releasing genes that had not circulated in humans for several decades, since the VLPs are not infectious, do not replicate, and cannot cause disease. The VLPs of the invention can also contain antigenic proteins from other infectious agents, thus allowing for the development of vaccines for other human or animal pathogens.

The present invention provides purified VLPs comprising at least one chimeric Orthomyxovirus membrane protein, wherein the VLP does not contain viral matrix or core protein. In another embodiment, the present invention provides purified VLPs comprising at least one chimeric influenza membrane protein, wherein the VLP does not contain an influenza matrix (M1) protein. A chimeric protein is a protein that contains a fragment of an Orthomyxovirus protein, e.g. influenza, fused to a heterologous protein. The heterologous protein may be a protein derived from another strain of influenza or a protein derived from another infectious agent. In one embodiment, said chimeric protein comprises the cytoplasmic tail of an influenza membrane protein fused to a heterologous protein. In another embodiment, said chimeric protein comprises the transmembrane domain of an influenza membrane protein fused to a heterologous protein. The cytoplasmic tails and transmembrane domains included in the chimeric proteins can be derived from influenza membrane proteins HA, NA, or M2. In another embodiment, the transmembrane domain and/or cytoplasmic tail of said influenza membrane proteins (e.g. HA and/or NA protein) extends from the N or C-terminus to approximately 0, 1, 2, 3 4, 5, 6, 7, 8, 9, 10, 11, 12, 13, 14, 15, 16, 17, 18, 19, 20 to about 50 amino acids past the transmembrane domain and is fused to said protein from another infectious agent. In another embodiment, the portion of the protein from another infectious agent that comprises a cytoplasmic and the transmembrane domain is replaced with a cytoplasmic and/or transmembrane domain from said influenza membrane protein (e.g. avian and/or seasonal influenza NA and/or HA). In another embodiment, said chimeric protein comprises a spacer between the cytoplasmic and/or transmembrane domain from said influenza protein and said heterologous protein. Said spacer can be approximately 0, 1, 2, 3 4, 5, 6, 7, 8, 9, 10, 11, 12, 13, 14, 15, 16, 17, 18, 19, 20 to about 50 amino acids. In another embodiment, said VLPs comprise different proteins from an infectious agent to make a multivalent VLP. One example includes a VLP comprising at least one RSV protein and at least one influenza protein. Many other combinations are possible.

Examples of cytoplasmic and/or transmembrane domains that can be fused to heterologous proteins are listed on Table 1 below. Note that these are only examples and are no way limited to those specific sequences. In a further embodiment, the cytoplasmic and/or transmembrane can be peptide fragments or peptide variants of said cytoplasmic and/or transmembrane. These fragments will retain the ability to drive VLP formation and/or drive a chimeric protein to the host's cell membrane. The peptide fragments are at least about 1, least about 2, least about 3, least about 4, at least 5, at least 6, at least 7, at least 8, at least 9, at least 10, at least 11, at least 12, at least 13, at least 14, at least 15, at least 20, at least 25, at least 30, at least 35, or at least about 40, at least about 50, at least about 55, at least about 60 or at least about 70 or more amino acids in length fused to the N and/or C terminus domain of a heterologous protein.

TABLE 1

Putative Cytoplasmic/Transmembrane domains of Influenza Proteins

| Influenza Protein | Transmembrane Domain | Cytoplasmic Domain | SEQ ID NO |
|---|---|---|---|
| HA | LSIYSTVASSLALAIMMAGLSLW | MCSNGSLQCRICI | 1 |
| M2 | PLTIAANIIGILHLTLWI | LDRLFFKCIYRRFKYGLKGGPSTEGVPK SMREEYRKEQQSAVDADDGHFVSIELE | 2 |
| NA | IITIGSICMVIGIVSLMLQIGNM | MNPNQK | 3 |

Methods to determine if cytoplasmic and/or transmembranes domains and/or their fragments fused to heterologous proteins will drive VLP formation and/or express said heterologous protein on the VLPs are known in the art and are described below. One example comprises seeding Sf9 cells (non-infected) into shaker flasks, allowing the cells to expand and infecting said cells with recombinant baculovirus comprising at least one chimeric protein described above. Once infection has occurred, the chimeric proteins are expressed from the recombinant baculovirus genome. If VLPs are formed, said VLPs can be isolated by passing the cell lysates from infected cells through a 20%-60% sucrose density gradient. Fractions in which VLPs are expected to equilibrate (30% sucrose fraction) can be run on an SDS-PAGE gel and subsequently analyzed by western blot with antibodies for the specific heterologous protein. A band on the western blot is an indication of VLP formation.

Some non-limiting examples of chimeric proteins of the invention include the cytoplasmic tail or transmembrane domain of influenza HA protein fused to a fragment of an antigenic heterologous protein, such as a glycoprotein from Varicella Zoster virus (gE, gI, gH, and gB), S protein from a coronavirus (an agent that causes SARS), a surface protein from Respiratory syncytial virus (F and G proteins), or a membrane protein (HA, NA, M2 proteins) from a different strain of influenza than the HA protein from which the cytoplasmic tail or transmembrane domain is derived. Other examples of infectious agents from which antigenic proteins can be derived to make chimeric proteins of the invention are listed below. In another embodiment, said VLP further comprises an enzymatically active influenza NA protein or homologous protein.

In another embodiment, said VLPs further comprise at least one additional protein from an infectious agent. Infectious agents can be viruses, bacteria, parasites and/or fungi. The proteins derived from these microorganisms can be expressed on the surface of the VLPs. These proteins can induce an immune response (cellular and/or humoral) in a vertebrate, which will prevent, treat, manage and/or ameliorate an infectious disease in said vertebrate. The infectious agent protein may be expressed as a chimeric protein comprising a cytoplasmic and/or transmembrane domain of an Orthomyxovirus protein. In another embodiment, the infectious agent protein may be expressed as a chimeric protein comprising a cytoplasmic and/or transmembrane domain of an influenza membrane protein as discussed above.

Non-limiting examples of viruses from which said infectious agent proteins can be derived from are the following: coronavirus (e.g. SARS), hepatitis viruses A, B, C, D & E3, human immunodeficiency virus (HIV), herpes viruses 1, 2, 6 & 7, cytomegalovirus, varicella zoster, papilloma virus, Epstein Barr virus, adenoviruses, bunya viruses (e.g. hanta virus), coxsakie viruses, picoma viruses, rotaviruses, rhinoviruses, rubella virus, mumps virus, measles virus, Rubella virus, polio virus (multiple types), adeno virus (multiple types), parainfluenza virus (multiple types), avian influenza (various types), shipping fever virus, Western and Eastern equine encephalomyelitis, Japanese encephalomyelitis, fowl pox, rabies virus, slow brain viruses, rous sarcoma virus, Papovaviridae, Parvoviridae, Picornaviridae, Poxyviridae (such as Smallpox or Vaccinia), Reoviridae (e.g., Rotavirus), Retroviridae (HTLV-I, HTLV-II, Lentivirus), Togaviridae (e.g., Rubivirus), Newcastle disease virus, West Nile fever virus, Tick borne encephalitis, yellow fever, chikungunya virus, respiratory syncytial virus, and dengue virus (all serotypes).

In another embodiment, the specific proteins from viruses may comprise: HA and/or NA from various strains of influenza virus (including avian), S protein from coronavirus, gp 160, gp140 and/or gp41 from HIV, F or G proteins from respiratory syncytial virus, E and preM/M from yellow fever virus, Dengue (all serotypes) or any flavivirus. Also included are any protein from a virus that can induce an immune response (cellular and/or humoral) in a vertebrate that can prevent, treat, manage and/or ameliorate an infectious disease in said vertebrate.

Non-limiting examples of bacteria from which said infectious agent proteins can be derived from are the following: *B. pertussis, Leptospira pomona, S. paratyphi* A and B, *C. diphtheriae, C. tetani, C. botulinum, C. perfringens, C. feseri* and other gas gangrene bacteria, *B. anthracis, P. pestis, P. multocida, Neisseria meningitidis, N. gonorrheae, Hemophilus influenzae, Actinomyces* (e.g., Norcardia), *Acinetobacter*, Bacillaceae (e.g., *Bacillus anthrasis*), Bacteroides (e.g., *Bacteroides fragilis*), Blastomycosis, Bordetella, Borrelia (e.g., *Borrelia burgdorferi*), Brucella, Campylobacter, Chlamydia, Coccidioides, Corynebacterium (e.g., *Corynebacterium diptheriae*), *E. coli* (e.g., Enterotoxigenic *E. coli* and Enterohemorrhagic *E. coli*), Enterobacter (e.g. *Enterobacter aerogenes*), Enterobacteriaceae (*Klebsiella, Salmonella* (e.g., *Salmonella typhi, Salmonella enteritidis, Serratia, Yersinia, Shigella*), Erysipelothrix, Haemophilus (e.g., *Haemophilus influenza* type B), Helicobacter, Legionella (e.g., *Legionella pneumophila*), Leptospira, Listeria (e.g., *Listeria monocytogenes*), Mycoplasma, Mycobacterium (e.g., *Mycobacterium leprae* and *Mycobacterium tuberculosis*), Vibrio (e.g., *Vibrio cholerae*), Pasteurellacea, Proteus, Pseudomonas (e.g., *Pseudomonas aeruginosa*), Rickettsiaceae, Spirochetes (e.g., *Treponema* spp., *Leptospira* spp., *Borrelia* spp.), *Shigella* spp., Meningiococcus, Pneumococcus and Streptococcus (e.g., *Streptococcus pneumoniae* and Groups A, B, and C Streptococci), Ureaplasmas. *Treponema pollidum, Staphylococcus aureus, Pasteurella haemolytica, Corynebacterium diptheriae* toxoid, Meningococcal polysaccharide, *Bordetella pertusis, Streptococcus pneumoniae, Clostridium tetani* toxoid, and *Mycobacterium bovis*.

Non-limiting examples of parasites from which said infectious agent proteins can be derived from are the following: leishmaniasis (*Leishmania tropica mexicana, Leishmania tropica, Leishmania major, Leishmania aethiopica, Leishmania braziliensis, Leishmania donovani, Leishmania infantum, Leishmania chagasi*), trypanosomiasis (*Trypanosoma brucei gambiense, Trypanosoma brucei rhodesiense*), toxoplasmosis (*Toxoplasma gondii*), schistosomiasis (*Schistosoma haematobium, Schistosoma japonicum, Schistosoma mansoni, Schistosoma mekongi, Schistosoma intercalatum*), malaria (*Plasmodium virax, Plasmodium falciparium, Plasmodium malariae* and *Plasmodium ovale*) Amebiasis (*Entamoeba histolytica*), Babesiosis (*Babesiosis microti*), Cryptosporidiosis (*Cryptosporidium parvum*), Dientamoebiasis (*Dientamoeba fragilis*), Giardiasis (*Giardia lamblia*), Helminthiasis and Trichomonas (*Trichomonas vaginalis*).

Non-limiting examples of fungi from which said infectious agent proteins can be derived are from the following: *Absidia* (e.g. *Absidia corymbifera*), *Ajellomyces* (e.g. *Ajellomyces capsulatus, Ajellomyces dermatitidis*), *Arthroderma* (e.g. *Arthroderma benhamiae, Arthroderma fulvum, Arthroderma gypseum, Arthroderma incurvatum, Arthroderma otae, Arthroderma vanbreuseghemii*), *Aspergillus* (e.g. *Aspergillus fumigatus, Aspergillus niger*), *Candida* (e.g. *Candida albicans, Candida albicans* var. *stellatoidea, Candida dublinensis, Candida glabrata, Candida guilliermondii* (*Pichia guilliermondii*), *Candida krusei* (*Issatschenkia orientalis*), *Candida parapsilosis, Candida pellicolosa* (*Pichia anomala*), *Candida tropicalis*), *Coccidioides* (e.g. *Coccidioides immitis*), *Cryptococcus* (e.g. *Cryptococcus neoformans* (*Filobasidiella neoformans*), *Histoplasma* (e.g. *Histoplasma capsulatum* (*Ajellomyces capsulatus*), *Microsporum* (e.g. *Microsporum canis* (*Arthroderma otae*), *Microsporum fulvum* (*Arthroderma fulvum*), *Microsporum gypseum*, Genus *Pichia* (e.g. *Pichia anomala, Pichia guilliermondii*), *Pneumocystis* (e.g. *Pneumocystis jirovecii*), *Cryptosporidium, Malassezia furfur, Paracoccidiodes*. The above lists are meant to be illustrative and by no means are meant to limit the invention to those particular bacterial, viral, fungal or parasitic organisms.

In another embodiment, said VLPs do not contain a viral matrix or core protein. A viral matrix protein is a protein that organizes and maintains virion structure. Viral matrix proteins usually interact directly with cellular membranes and can be involved in the budding process. Viral core proteins are proteins that make up part of the nucelocapsid and typically are directly associated with the viral nucleic acid. Examples include RSV M and retrovirus gag proteins.

The invention also provides a purified VLP comprising at least one influenza membrane protein, wherein the VLP does not contain an influenza matrix (M1) protein. In one embodiment, said VLP further comprises at least one additional protein from an infectious agent. In another embodiment, said influenza membrane protein is HA. In another embodiment, said HA is a seasonal or avian HA. In another embodiment, said VLP does not contain a viral matrix or core protein. The influenza membrane proteins include HA, NA, and M2 and can be derived from influenza B or any strain of influenza A.

In another embodiment, said VLP further comprises an influenza NA protein. The NA protein and at least one influenza membrane protein can either be derived from the same influenza strain or derived from different strains. In some embodiments, said VLP comprises a HA from an avian, pandemic and/or seasonal influenza virus and a NA from an avian, pandemic and/or seasonal influenza virus, wherein said HA is selected from the group consisting of H1, H2, H3, H4, H5, H6, H7, H8, H9, H10, H11, H12, H13, H14, H15 and H16 and said NA is selected from the group consisting of N1, N2, N3, N4, N5, N6, N7, N8 and N9. In one embodiment, said VLP comprises HA and NA proteins, which are both derived from the influenza H5N1 virus subtype. In other embodiments, said HA and NA proteins are derived from different influenza subtypes. In another embodiment, said NA protein has enzymatic activity.

The invention also encompasses variants of the said influenza proteins and chimeric proteins expressed on or in the VLPs of the invention. The variants may contain alterations in the amino acid sequences of the constituent proteins. The term "variant" with respect to a polypeptide refers to an amino acid sequence that is altered by one or more amino acids with respect to a reference sequence. The variant can have "conservative" changes, wherein a substituted amino acid has similar structural or chemical properties, e.g., replacement of leucine with isoleucine. Alternatively, a variant can have "nonconservative" changes, e.g., replacement of a glycine with a tryptophan. Analogous minor variations can also include amino acid deletion or insertion, or both. Guidance in determining which amino acid residues can be substituted, inserted, or deleted without eliminating biological or immunological activity can be found using computer programs well known in the art, for example, DNASTAR software.

Natural variants can occur due to antigenic drifts. Antigenic drifts are small changes in the viral proteins that happen continually over time. Thus, a person infected with a particular flu virus strain develops antibody against that virus, as newer virus strains appear, the antibodies against the older strains no longer recognize the newer virus and reinfection can occur. This is why there is a new vaccine for influenza each season. In addition, some changes in an influenza virus can cause influenza virus to cross species. For example, some avian influenza viruses developed genetic variations associated with the capability of crossing the species barrier. Such a virus is capable of causing a pandemic because people have no natural immunity to the virus and the virus can easily spread from person to person. These naturally occurring variations of the influenza proteins are an embodiment of the invention.

General texts which describe molecular biological techniques, which are applicable to the present invention, such as cloning, mutation, cell culture and the like, include Berger and Kimmel, Guide to Molecular Cloning Techniques, Methods in Enzymology volume 152 Academic Press, Inc., San Diego, Calif. (Berger); Sambrook et al., Molecular Cloning—A Laboratory Manual (3rd Ed.), Vol. 1-3, Cold Spring Harbor Laboratory, Cold Spring Harbor, N.Y., 2000 ("Sambrook") and Current Protocols in Molecular Biology, F. M. Ausubel et al., eds., Current Protocols, a joint venture between Greene Publishing Associates, Inc. and John Wiley & Sons, Inc., ("Ausubel"). These texts describe mutagenesis, the use of vectors, promoters and many other relevant topics related to, e.g., the cloning and mutation of influenza proteins or fragments thereof. Thus, the invention also encompasses using known methods of protein engineering and recombinant DNA technology to improve or alter the characteristics of the influenza proteins expressed on or in the VLPs of the invention. Various types of mutagenesis can be used to produce and/or isolate variant influenza proteins or antigenic proteins derived from other infectious agents and/or to further modify/mutate the polypeptides of the invention. They include but are not limited to site-directed, random point mutagenesis, homologous recombination (DNA shuffling), mutagenesis using uracil containing templates, oligonucleotide-directed mutagenesis, phosphorothioate-modified DNA mutagenesis, mutagenesis using gapped duplex DNA or the like. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the present invention. In one embodiment, mutagenesis can be guided by known information of the naturally occurring molecule or altered or mutated naturally occurring molecule, e.g., sequence, sequence comparisons, physical properties, crystal structure or the like.

The invention further comprises influenza protein variants which show substantial biological activity, e.g., able to elicit an effective antibody response when expressed on or in a VLP. Such variants include deletions, insertions, inversions, repeats, and substitutions selected according to general rules known in the art so as to have little effect on activity.

Methods of cloning said influenza proteins are known in the art. For example, the influenza gene encoding a specific influenza protein can be isolated by RT-PCR from polyadenylated mRNA extracted from cells which had been infected with an influenza virus. The resulting product gene can be cloned as a DNA insert into a vector. The term "vector" refers to the means by which a nucleic acid can be propagated and/or transferred between organisms, cells, or cellular components. Vectors include plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. In many, but not all, common embodiments, the vectors of the present invention are plasmids or bacmids.

Thus, the invention comprises nucleotides that encode influenza membrane proteins, including chimeric molecules, cloned into an expression vector that can be expressed in a cell that induces the formation of VLPs of the invention. An "expression vector" is a vector, such as a plasmid that is capable of promoting expression, as well as replication of a nucleic acid incorporated therein. Typically, the nucleic acid to be expressed is "operably linked" to a promoter and/or enhancer, and is subject to transcription regulatory control by the promoter and/or enhancer. In one embodiment, said nucleotides encode for a chimeric protein (as discussed above). In another embodiment, said vector comprises nucleotides that encode the HA and/or NA influenza membrane proteins. In another embodiment, said vector comprises nucleotides that encode the M2 influenza membrane protein. In another embodiment, said vector comprises nucleotides that encode a chimeric protein and an antigenic protein from another infectious agent. In another embodiment, said vector comprises nucleotides that encode HA protein and an antigenic protein from another infectious agent. In a preferred embodiment, the expression vector is a baculovirus vector. After the nucleotides encoding said influenza proteins or chimeric proteins have been cloned, said nucleotides can be further manipulated. For example, a person with skill in the art can mutate specific bases in the coding region to produce variants. The variants may contain alterations in the coding regions, non-coding regions, or both. Such variants may increase the immunogenicity of an influenza protein or chimeric protein or remove a splice site from a protein or RNA. For example, in one embodiment, the HA is engineered to remove or mutate the cleavage site. For example, wild type H5 HA has a cleavage site that contains multiple basic amino acids (RRRKR (SEQ ID NO. 5)). This wild type sequence makes the HA more susceptible to multiple ubiquitous proteases that may be present in host cells or systems expressing these HAs. In one embodiment, removing these amino acids can reduce the susceptibility of the HA to various proteases. In another embodiment, the cleavage site can be mutated to remove the cleavage site (e.g. mutate to RESR (SEQ ID NO. 6)).

In some embodiments, mutations can be made which produce silent substitutions, additions, or deletions, but do not alter the properties or activities of the encoded protein or how the proteins are made. Nucleotide variants can be produced for a variety of reasons, e.g., to optimize codon expression for a particular host (change codons in the human mRNA to those preferred by insect cells such as Sf9 cells). See U.S. patent publication 2005/0118191, herein incorporated by reference in its entirety for all purposes.

In addition, the nucleotides can be sequenced to ensure that the correct coding regions were cloned and do not contain any unwanted mutations. The nucleotides can be subcloned into an expression vector (e.g. baculovirus) for expression in any cell. The above is only one example of how the influenza viral proteins can be cloned. A person with skill in the art understands that additional methods are available and are possible.

The invention also provides for constructs and/or vectors that comprise nucleotides that encode for influenza genes, including HA, NA, M2, or portions thereof, and/or any chimeric molecule described above. The vector may be, for example, a phage, plasmid, viral, or retroviral vector. The constructs and/or vectors that encode influenza viral genes, including HA, NA, M2, or portions thereof, and/or any chimeric molecule described above, should be operatively linked to an appropriate promoter, such as the AcMNPV polyhedrin promoter (or other baculovirus promoter), phage lambda PL promoter, the E. coli lac, phoA and tac promoters, the SV40 early and late promoters, and promoters of retroviral LTRs are non-limiting examples. Other suitable promoters will be known to the skilled artisan depending on the host cell and/or the rate of expression desired. The expression constructs will further contain sites for transcription initiation, termination, and, in the transcribed region, a ribosome binding site for translation. The coding portion of the transcripts expressed by the constructs will preferably include a translation initiating codon at the beginning and a termination codon appropriately positioned at the end of the polypeptide to be translated.

The expression vectors will preferably include at least one selectable marker. Such markers include dihydrofolate reductase, G418 or neomycin resistance for eukaryotic cell culture and tetracycline, kanamycin or ampicillin resistance genes for culturing in E. coli and other bacteria. Among vectors preferred are virus vectors, such as baculovirus, poxvirus (e.g., vaccinia virus, avipox virus, canarypox virus, fowlpox virus, raccoonpox virus, swinepox virus, etc.), adenovirus (e.g., canine adenovirus), herpesvirus, and retrovirus. Other vectors that can be used with the invention comprise vectors for use in bacteria, which include pQE70, pQE60 and pQE-9, pBluescript vectors, Phagescript vectors, pNH8A, pNH16a, pNH18A, pNH46A, ptrc99a, pKK223-3, pKK233-3, pDR540, and pRIT5. Among preferred eukaryotic vectors are pFastBacl pWINEO, pSV2CAT, pOG44, pXT1 and pSG, pSVK3, pBPV, pMSG, and pSVL. Other suitable vectors will be readily apparent to the skilled artisan. In one embodiment, said vector that comprises nucleotides encoding for influenza viral genes, including HA, NA, M2, or portions thereof, and/or any chimeric molecule, is pFastBac.

Next, the recombinant vector can be transfected, infected, or transformed into a suitable host cell. Thus, the invention provides for host cells which comprise a vector (or vectors) that contain nucleic acids which code for HA, NA, M2, or any chimeric molecule described above and permit the expression of those genes in said host cell under conditions which allow the formation of VLPs.

In one embodiment, the recombinant constructs mentioned above could be used to transfect, infect, or transform eukaryotic cells and/or prokaryotic cells to express HA, NA, M2, or any chimeric protein described above. Among eukaryotic host cells are yeast, insect, avian, plant, C. elegans (or nematode) and mammalian host cells. Non limiting examples of insect cells are, Spodoptera frugiperda (Sf) cells, e.g. Sf9, Sf21, Trichoplusia ni cells, e.g. High Five cells, and Drosophila S2 cells. Examples of fungi (including yeast) host cells are S. cerevisiae, Kluyveromyces lactis (K. lactis), species of Candida including C. albicans and C. glabrata, Aspergillus nidulans, Schizosaccharomyces pombe (S. pombe), Pichia pastoris, and Yarrowia lipolytica. Examples of mammalian cells are COS cells, baby hamster kidney cells, mouse L cells, LNCaP cells, Chinese hamster ovary (CHO) cells, human embryonic kidney (HEK) cells, and African green monkey cells, CV1 cells, HeLa cells, MDCK cells, Vero and Hep-2 cells. Xenopus laevis oocytes, or other cells of amphibian origin, may also be used. Prokaryotic host cells include bacterial cells, for example, E. coli, B. subtilis, and mycobacteria.

Vectors, e.g., vectors comprising HA, NA, M2 or chimeric polynucleotides, can be transfected into host cells according to methods well known in the art. For example, introducing nucleic acids into eukaryotic cells can be by calcium phosphate co-precipitation, electroporation, microinjection, lipofection, and transfection employing polyamine transfection reagents. In one embodiment, the said vector is a recombinant baculovirus. In another embodiment, said recombinant baculovirus is transfected into a eukaryotic cell. In a preferred embodiment, said cell is an insect cell. In another embodiment, said insect cell is a Sf9 cell.

In another embodiment, said vector and/or host cell comprise nucleotides which encode an avian, pandemic and/or seasonal influenza virus HA protein selected from the group consisting of H1, H2, H3, H4, H5, H6, H7, H8, H9, H10, H11, H12, H13, H14, H15 and H16. In another embodiment, said vector and/or host cells comprise nucleotides which encode an NA protein which is selected from the group consisting of N1, N2, N3, N4, N5, N6, N7, N8 and N9. In another embodiment, said vector and/or host cell comprises influenza HA, and/or NA. In another embodiment, said vector and/or host cell comprises influenza HA, NA, and an antigenic protein from another infectious agent. In another embodiment, said vector and/or host cell comprises at least one chimeric protein described above. These vector and/or host cells do not contain influenza M1 protein or any other viral matrix or core proteins.

This invention also provides for constructs and methods that will increase the efficiency of VLP production. For example, the nucleotides that encode HA, NA, M2, or chimeric proteins can be codon optimized for a specific cell type. For example, nucleic acids can be codon optimized for expression in Sf9 cells (see U.S. patent publication 2005/0118191, herein incorporated by reference in its entirety for all purposes).

The invention includes methods of making VLPs comprising expressing a chimeric protein or an influenza membrane protein in a cell, wherein the cell does not contain or express an influenza matrix (M1) protein; and purifying the VLPs. Depending on the expression system and host cell selected, the VLPs are produced by growing host cells transformed by an expression vector under conditions whereby the recombinant proteins are expressed and VLPs are formed. The selection of the appropriate growth conditions is within the ordinary skill in the art.

Methods to grow cells engineered to produce VLPs of the invention include, but are not limited to, batch, batch-fed, continuous and perfusion cell culture techniques. Cell culture means the growth and propagation of cells in a bioreactor (a fermentation chamber) where cells propagate and express protein (e.g. recombinant proteins) for purification and isolation. Typically, cell culture is performed under sterile, controlled temperature and atmospheric conditions in a bioreactor. A bioreactor is a chamber used to culture cells in which environmental conditions such as temperature, atmosphere, agitation and/or pH can be monitored. In one embodiment, said bioreactor is a stainless steel chamber. In another embodiment, said bioreactor is a pre-sterilized plastic bag (e.g. Cellbag®, Wave Biotech, Bridgewater, N.J.). In other embodiment, said pre-sterilized plastic bags are about 50 L to 1000 L bags.

The VLPs are then isolated using methods that preserve the integrity thereof, such as by gradient centrifugation, e.g., cesium chloride, sucrose and iodixanol, as well as standard purification techniques including, e.g., ion exchange and gel filtration chromatography.

The following is an example of how VLPs of the invention may be made, isolated and purified. Usually VLPs are produced from recombinant cell lines engineered to create a VLP when said cells are grown in cell culture (see above). Production of VLPs may be accomplished as illustrated in the Examples. A person of skill in the art would understand that there are additional methods that can be utilized to make and purify VLPs of the invention, thus the invention is not limited to the method described.

Production of VLPs of the invention can start by seeding Sf9 cells (non-infected) into shaker flasks, allowing the cells to expand and scaling up as the cells grow and multiply (for example from a 125-ml flask to a 50 L Wave bag). The medium used to grow the cells is formulated for the appropriate cell line (preferably serum free media, e.g. insect medium ExCell-420, JRH). Next, said cells are infected with recombinant baculovirus at the most efficient multiplicity of infection (e.g. from about 1 to about 3 plaque forming units per cell). Once infection has occurred, the chimeric proteins or HA, NA or M2 proteins are expressed from the recombinant baculovirus genome, self assemble into VLPs and are secreted from the cells approximately 24 to 72 hours post infection. Usually, infection is most efficient when the cells are in mid-log phase of growth ($4-8 \times 10^6$ cells/ml) and are at least about 90% viable.

VLPs of the invention can be harvested approximately 48 to 96 hours post infection, when the levels of VLPs in the cell culture medium are near the maximum but before extensive cell lysis. The Sf9 cell density and viability at the time of harvest can be about $0.5 \times 10^6$ cells/ml to about $1.5 \times 10^6$ cells/ml with at least 20% viability, as shown by dye exclusion assay. Next, the medium is removed and clarified. NaCl can be added to the medium to a concentration of about 0.4 to about 1.0 M, preferably to about 0.5 M, to avoid VLP aggregation. The removal of cells and cellular debris from the cell culture medium containing VLPs of the invention can be accomplished by tangential flow filtration (TFF) with a single use, pre-sterilized hollow fiber 0.5 or 1.00 μm filter cartridge or a similar device.

Next, VLPs in the clarified culture medium can be concentrated by ultrafiltration using a disposable, pre-sterilized 500,000 molecular weight cut off hollow fiber cartridge. The concentrated VLPs can be diafiltrated against 10 volumes pH 7.0 to 8.0 phosphate-buffered saline (PBS) containing 0.5 M NaCl to remove residual medium components.

The concentrated, diafiltered VLPs can be furthered purified on a 20% to 60% discontinuous sucrose gradient in pH 7.2 PBS buffer with 0.5 M NaCl by centrifugation at 6,500×g for 18 hours at about 4° C. to about 10° C. Usually VLPs will form a distinctive visible band between about 30% to about 40% sucrose or at the interface (in a 20% and 60% step gradient) that can be collected from the gradient and stored. This product can be diluted to comprise 200 mM of NaCl in preparation for the next step in the purification process. This product contains VLPs and may contain intact baculovirus particles.

Further purification of VLPs can be achieved by anion exchange chromatography, or 44% isopycnic sucrose cushion centrifugation. In anion exchange chromatography, the sample from the sucrose gradient (see above) is loaded into column containing a medium with an anion (e.g. Matrix Fractogel EMD TMAE) and eluded via a salt gradient (from about 0.2 M to about 1.0 M of NaCl) that can separate the VLP from other contaminates (e.g. baculovirus and DNA/RNA). In the sucrose cushion method, the sample comprising the VLPs is added to a 44% sucrose cushion and centrifuged for about 18 hours at 30,000 g. VLPs form a band at the top of 44% sucrose, while baculovirus precipitates at the bottom and other contaminating proteins stay in the 0% sucrose layer at the top. The VLP peak or band is collected.

The intact baculovirus can be inactivated, if desired. Inactivation can be accomplished by chemical methods, for example, formalin or β-propyl lactone (BPL). Removal and/or inactivation of intact baculovirus can also be largely accomplished by using selective precipitation and chromatographic methods known in the art, as exemplified above. Methods of inactivation comprise incubating the sample containing the VLPs in 0.2% of BPL for 3 hours at about 25° C. to about 27° C. The baculovirus can also be inactivated by incubating the sample containing the VLPs at 0.05% BPL at 4° C. for 3 days, then at 37° C. for one hour.

After the inactivation/removal step, the product comprising VLPs can be run through another diafiltration step to remove any reagent from the inactivation step and/or any residual sucrose, and to place the VLPs into the desired buffer (e.g. PBS). The solution comprising VLPs can be sterilized by methods known in the art (e.g. sterile filtration) and stored in the refrigerator or freezer.

The above techniques can be practiced across a variety of scales. For example, T-flasks, shake-flasks, spinner bottles, up to industrial sized bioreactors. The bioreactors can comprise either a stainless steel tank or a pre-sterilized plastic bag (for example, the system sold by Wave Biotech, Bridgewater, N.J.). A person with skill in the art will know what is most desirable for their purposes.

Expansion and production of baculovirus expression vectors and infection of cells with recombinant baculovirus to produce recombinant influenza VLPs can be accomplished in insect cells, for example Sf9 insect cells as previously described. In a preferred embodiment, the cells are SF9 infected with recombinant baculovirus engineered to produce influenza VLPs.

Pharmaceutical or Vaccine Formulations and Administration

The pharmaceutical compositions useful herein contain a pharmaceutically acceptable carrier, including any suitable diluent or excipient, which includes any pharmaceutical agent that does not itself induce the production of an immune response harmful to the vertebrate receiving the composition, and which may be administered without undue toxicity and a VLP of the invention. As used herein, the term "pharmaceutically acceptable" means being approved by a regulatory agency of the Federal or a state government or listed in the U.S. Pharmacopia, European Pharmacopia or other generally recognized pharmacopeia for use in vertebrates, and more particularly in humans. These compositions can be useful as a vaccine and/or antigenic compositions for inducing a protective immune response in a vertebrate.

The invention provides a vaccine comprising VLPs that comprise at least one influenza membrane protein, but do not contain an influenza matrix (M1) protein. In one embodiment, said influenza membrane protein is HA. In another embodiment, said HA protein is a seasonal or avian HA. In another embodiment, said vaccine comprises VLPs further comprising at least one antigenic protein from an infectious agent. In another embodiment, said vaccine comprises VLPs further comprising influenza NA protein. In another embodiment, said vaccine comprises VLPs comprising HA and NA proteins derived from the influenza H5N1 subtype.

The invention also provides a vaccine comprising VLPs that comprise at least one chimeric protein, but do not contain an influenza matrix (M1) protein. In one embodiment, the vaccine comprises VLPs comprising a chimeric protein, wherein the chimeric protein contains the cytoplasmic tail of an influenza membrane protein. In another embodiment, said membrane protein is HA. In another embodiment, said membrane protein is NA. In another embodiment, said membrane protein is M2. In another embodiment, said vaccine comprises VLPs further comprising at least one antigenic protein from an infectious agent. In another embodiment, said vaccine comprises VLPs comprising a chimeric protein, wherein the chimeric protein contains the transmembrane domain of an influenza membrane protein. In another embodiment, said membrane protein is HA.

The invention includes an antigenic formulation comprising VLPs that comprise at least one influenza membrane protein, but do not contain an influenza matrix (M1) protein. In one embodiment, said influenza membrane protein is HA. In another embodiment, said HA protein is a seasonal or avian HA. In another embodiment, said antigenic formulation comprises VLPs further comprising at least one antigenic protein from an infectious agent. In another embodiment, said antigenic formulation comprises VLPs further comprising influenza NA protein. In another embodiment, said antigenic formulation comprises VLPs comprising HA and NA proteins derived from the influenza H5N1 subtype.

The invention also includes an antigenic formulation comprising VLPs that comprise at least one chimeric protein, but do not contain an influenza matrix (M1) protein. In one embodiment, the antigenic formulation comprises VLPs comprising a chimeric protein, wherein the chimeric protein contains the cytoplasmic tail of an influenza membrane protein. In another embodiment, said membrane protein is HA. In another embodiment, said membrane protein is NA. In another embodiment, said membrane protein is M2. In another embodiment, said antigenic formulation comprises VLPs further comprising at least one antigenic protein from an infectious agent. In another embodiment, said antigenic formulation comprises VLPs comprising a chimeric protein, wherein the chimeric protein contains the transmembrane domain of an influenza membrane protein. In another embodiment, said membrane protein is HA.

Said pharmaceutical formulations of the invention comprise VLPs comprising an influenza HA, NA, or M2 protein or any chimeric molecule described above and a pharmaceutically acceptable carrier or excipient. Pharmaceutically acceptable carriers include but are not limited to saline, buffered saline, dextrose, water, glycerol, sterile isotonic aqueous buffer, and combinations thereof. A thorough discussion of pharmaceutically acceptable carriers, diluents, and other excipients is presented in Remington's Pharmaceutical Sciences (Mack Pub. Co. N.J. current edition). The formulation should suit the mode of administration. In a preferred embodiment, the formulation is suitable for administration to humans, preferably is sterile, non-particulate and/or non-pyrogenic.

In another embodiment, different chimeric VLPs are blended together to create a multivalent formulation. These VLPs may comprise VLPs HA and/or NA from different strains of influenza virus (e.g. influenza A and/or influenza B) or chimeric protein from different infectious agents (e.g. RSV, coronavirus, HIV). One example includes a formulation comprising VLPs which comprising at least one RSV protein and at least one influenza protein. Many other combinations are possible.

The composition, if desired, can also contain minor amounts of wetting or emulsifying agents, or pH buffering agents. The composition can be a solid form, such as a lyophilized powder suitable for reconstitution, a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

The invention provides that the VLP formulation be packaged in a hermetically sealed container such as an ampoule or sachette indicating the quantity of composition. In one embodiment, the VLP composition is supplied as a liquid, in another embodiment, as a dry sterilized lyophilized powder or water free concentrate in a hermetically sealed container and can be reconstituted, e.g., with water or saline to the appropriate concentration for administration to a subject.

In an alternative embodiment, the VLP composition is supplied in liquid form in a hermetically sealed container indicating the quantity and concentration of the VLP composition. Preferably, the liquid form of the VLP composition is supplied in a hermetically sealed container at least about 50 µg/ml, more preferably at least about 100 µg/ml, at least about 200 µg/ml, at least 500 µg/ml, or at least 1 mg/ml.

Generally, VLPs of the invention are administered in an effective amount or quantity sufficient to stimulate an immune response against one or more strains of influenza or another infectious agent from which the antigenic protein contained within the VLP is derived. Preferably, administration of the VLP of the invention elicits immunity against influenza. Typically, the dose can be adjusted within this range based on, e.g., age, physical condition, body weight, sex, diet, time of administration, and other clinical factors. The prophylactic vaccine formulation is systemically administered, e.g., by subcutaneous or intramuscular injection using a needle and syringe, or a needle-less injection device. Alternatively, the vaccine formulation is administered intranasally, either by drops, large particle aerosol (greater than about 10 microns), or spray into the upper respiratory tract. While any of the above routes of delivery results in an immune response, intranasal administration confers the added benefit of eliciting mucosal immunity at the site of entry of many viruses, including influenza.

Thus, the invention also comprises a method of formulating a vaccine or antigenic composition that induces immunity to an infection or at least one symptom thereof to a mammal, comprising adding to said formulation an effective dose of a VLP of the invention. In one embodiment, said infection is an influenza infection. An "effective dose" generally refers to the amount of VLPs of the invention sufficient to induce immunity, to prevent and/or ameliorate an infection or to reduce at least one symptom of an infection and/or to enhance the efficacy of another dose of a VLP. An effective dose may refer to the amount of VLPs sufficient to delay or minimize the onset of an infection. An effective dose may also refer to the amount of VLPs that provide a therapeutic benefit in the treatment or management of an infection. Further, an effective dose is the amount with respect to VLPs of the invention alone, or in combination with other therapies, that provides a therapeutic benefit in the treatment or management of an infection. An effective dose may also be the amount sufficient to enhance a subject's (e.g., a human's) own immune response against a subsequent exposure to an infectious agent. Levels of immunity can be monitored, e.g., by measuring amounts of neutralizing secretory and/or serum antibodies, e.g., by plaque neutralization, complement fixation, enzyme-linked immunosorbent, or microneutralization assay. In the case of a vaccine, an "effective dose" is one that prevents disease and/or reduces the severity of symptoms.

While stimulation of immunity with a single dose is preferred, additional dosages can be administered, by the same or different route, to achieve the desired effect. In neonates and infants, for example, multiple administrations may be required to elicit sufficient levels of immunity. Administration can continue at intervals throughout childhood, as necessary to maintain sufficient levels of protection against infections, e.g. influenza infection. Similarly, adults who are particularly susceptible to repeated or serious infections, such as, for example, health care workers, day care workers, family members of young children, the elderly, and individuals with compromised cardiopulmonary function may require multiple immunizations to establish and/or maintain protective immune responses. Levels of induced immunity can be monitored, for example, by measuring amounts of neutralizing secretory and serum antibodies, and dosages adjusted or vaccinations repeated as necessary to elicit and maintain desired levels of protection.

Methods of administering a composition comprising VLPs (vaccine and/or antigenic formulations) include, but are not limited to, parenteral administration (e.g., intradermal, intramuscular, intravenous and subcutaneous), epidural, and mucosal (e.g., intranasal and oral or pulmonary routes or by suppositories). In a specific embodiment, compositions of the present invention are administered orally, intradermally, intranasally, intramuscularly, intraperitoneally, intravenously, or subcutaneously. The compositions may be administered by any convenient route, for example by infusion or bolus injection, by absorption through epithelial or mucocutaneous linings (e.g., oral mucous, colon, conjunctiva, nasopharynx, oropharynx, vagina, urethra, urinary bladder and intestinal mucosa, etc.) and may be administered together with other biologically active agents. In some embodiments, intranasal or other mucosal routes of administration of a composition comprising VLPs of the invention may induce an antibody or other immune response that is substantially higher than other routes of administration. In another embodiment, intranasal or other mucosal routes of administration of a composition comprising VLPs of the invention may induce an antibody or other immune response that will induce cross protection against other strains of influenza. Administration can be systemic or local.

Vaccines and/or antigenic formulations of the invention may also be administered on a dosage schedule, for example, an initial administration of the vaccine composition with subsequent booster administrations. In particular embodiments, a second dose of the composition is administered anywhere from two weeks to one year, preferably from about 1, about 2, about 3, about 4, about 5 to about 6 months, after the initial administration. Additionally, a third dose may be administered after the second dose and from about three months to about two years, or even longer, preferably about 4, about 5, or about 6 months, or about 7 months to about one year after the initial administration. The third dose may be optionally administered when no or low levels of specific immunoglobulins are detected in the serum and/or urine or mucosal secretions of the subject after the second dose. In a preferred embodiment, a second dose is administered about one month after the first administration and a third dose is administered about six months after the first administration. In another embodiment, the second dose is administered about six months after the first administration. In another embodiment, said VLPs of the invention can be administered as part of a combination therapy. For example, VLPs of the invention can be formulated with other immunogenic compositions, antivirals and/or antibiotics.

The dosage of the pharmaceutical formulation can be determined readily by the skilled artisan, for example, by first identifying doses effective to elicit a prophylactic or therapeutic immune response, e.g., by measuring the serum titer of virus specific immunoglobulins or by measuring the inhibitory ratio of antibodies in serum samples, or urine samples, or mucosal secretions. Said dosages can be determined from animal studies. A non-limiting list of animals used to study the efficacy of vaccines include the guinea pig, hamster, ferrets, chinchilla, mouse and cotton rat. Most animals are not natural hosts to infectious agents but can still serve in studies of various aspects of the disease. For example, any of the above animals can be dosed with a vaccine candidate, e.g. VLPs of the invention, to partially characterize the immune response induced, and/or to determine if any neutralizing antibodies have been produced. For example, many studies have been conducted in the mouse model because mice are small in size and their low cost allows researchers to conduct studies on a larger scale.

In addition, human clinical studies can be performed to determine the preferred effective dose for humans by a skilled artisan. Such clinical studies are routine and well known in the art. The precise dose to be employed will also depend on the route of administration. Effective doses may be extrapolated from dose-response curves derived from in vitro or animal test systems.

As also well known in the art, the immunogenicity of a particular composition can be enhanced by the use of non-specific stimulators of the immune response, known as adjuvants. Adjuvants have been used experimentally to promote a generalized increase in immunity against unknown antigens (e.g., U.S. Pat. No. 4,877,611). Immunization protocols have used adjuvants to stimulate responses for many years, and as such, adjuvants are well known to one of ordinary skill in the art. Some adjuvants affect the way in which antigens are presented. For example, the immune response is increased when protein antigens are precipitated by alum. Emulsification of antigens also prolongs the duration of antigen presentation. The inclusion of any adjuvant described in Vogel et al., "A Compendium of Vaccine Adjuvants and Excipients ($2^{nd}$ Edition)," herein incorporated by reference in its entirety for all purposes, is envisioned within the scope of this invention.

Exemplary, adjuvants include complete Freund's adjuvant (a non-specific stimulator of the immune response containing killed *Mycobacterium tuberculosis*), incomplete Freund's adjuvants and aluminum hydroxide adjuvant. Other adjuvants comprise GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion also is contemplated. MF-59, Novasomes®, MHC antigens may also be used.

The VLPs of the invention can also be formulated with "immune stimulators." The term "immune stimulator" refers to a compound that enhances an immune response via the body's own chemical messengers (cytokines). These molecules comprise various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc. The immune stimulator molecules can be administered in the same formulation as VLPs of the invention, or can be administered separately. Either the protein or an expression vector encoding the protein can be administered to produce an immunostimulatory effect. Thus in one embodiment, the invention comprises antigenic and vaccine formulations comprising an adjuvant and/or an immune stimulator.

Methods of Stimulating an Immune Response

The VLPs of the invention are useful for preparing compositions that stimulate an immune response that confers immunity or substantial immunity to infectious agents. Both mucosal and cellular immunity may contribute to immunity to infectious agents and disease. Antibodies secreted locally in the upper respiratory tract are a major factor in resistance to natural infection. Secretory immunoglobulin A (sIgA) is involved in protection of the upper respiratory tract and serum IgG in protection of the lower respiratory tract. Protection of the respiratory tract is important in the case of influenza and other infections that are transmissible through the respiratory system. The immune response induced by an infection protects against reinfection with the same virus or an antigenically similar viral strain.

VLPs of the invention can stimulate the production of antibodies that, for example, neutralize infectious agents, block infectious agents from entering cells, block replication of said infectious agents, and/or protect host cells from infection and destruction resulting in a "protective immune response". A protective immune response can also refer to an immune response that is mediated by T-lymphocytes and/or other white blood cells against an infectious agent, exhibited by a vertebrate (e.g., a human), that prevents or ameliorates infection (e.g. influenza infection) or reduces at least one symptom thereof.

Recently there has been a concerted effort to create a vaccine against avian influenza virus that has the potential to create a pandemic. That is because a number of avian influenza viruses have crossed the species barrier and directly infected humans resulting in illness and, in some cases, death. These viruses were H5N1, H9N2 and H7N7 (Cox et al., 2004). A recent study examined the potential of using inactivated H5N1 influenza virus as a vaccine. The formulation of the vaccine was similar to the licensed inactivated vaccines currently licensed for marketing. The study concluded that using inactivated H5N1 virus did induce an immune response in humans, however the dose given was very high (90 μg of avian influenza compared to 15 μg of the licensed vaccine) (Treanor et al., 2006). This high amount of avian influenza antigen is impractical for a worldwide vaccination campaign. The VLPs of the invention can induce an immune response in a vertebrate when administered to said vertebrate, and may be more efficient in inducing immunity than inactivated virus.

In addition to the trepidation of infection with potentially pandemic avian influenza viruses, frequent mutations in influenza viral antigens that create new variants or viral strains is problematic when attempting to develop vaccines to protect the public from influenza infection. One approach to solve this problem is to administer seasonal influenza vaccines to humans every year to reduce the incidence of influenza cases. At present, there are two subtypes of influenza A and influenza B circulating in the United States. Current vaccines are, therefore, trivalent to provide protection against the strains currently circulating. Each year a different strain or variation of an influenza virus changes. Thus, for most years a new vaccine composition is manufactured and administered. Inactivated vaccines are produced by propagation of the virus in embryonated hens' eggs. The allantoic fluid is harvested, and the virus is concentrated and purified, then inactivated. Thus, the current licensed influenza virus vaccines may contain trace amounts of residual egg proteins and, therefore, should not be administered to persons who have anaphylactic hypersensitivity to eggs. In addition, supplies of eggs must be organized and strains for vaccine production must be selected months in advance of the next influenza season, thus limiting the flexibility of this approach and often resulting in delays and shortages in production and distribution. In addition, some influenza strains do not replicate well in embryonated chicken eggs which may limit the influenza strains which can be grown and formulated into vaccines. VLPs of the invention do not require eggs for production, as they are made via a cell culture system. This feature of the VLPs combined with the ease with which the VLPs can be made to contain emerging variants of the influenza antigenic proteins could potentially make influenza vaccine production more efficient and accessible to a greater portion of the population.

Thus, the invention encompasses a method of inducing protective immunity to an infection in a subject, comprising administering to the subject an antigenic formulation or vaccine comprising VLPs, wherein said VLPs comprise at least one chimeric protein, but does not include an influenza matrix (M1) protein. In one embodiment, said VLPs further comprise at least one additional protein from an infectious agent. In another embodiment, said chimeric protein contains the cytoplasmic tail of an influenza membrane protein. In another embodiment, said influenza membrane protein is HA, NA, or M2. In another embodiment, said chimeric protein contains the transmembrane domain of an influenza membrane protein. In another embodiment, said influenza membrane protein is HA. In another embodiment, said VLPs do not contain a viral matrix or core protein. The chimeric proteins may contain the extracellular domains of antigenic proteins, such as HA and NA, from different viral strains than that from which the cytoplasmic tail or transmembrane domains are derived. For illustration purposes, one possible chimeric protein of the invention could contain the extracellular domain from a HA protein from an avian influenza virus (e.g. H5) fused to a cytoplasmic tail from a HA protein from a seasonal influenza virus. VLPs comprising multiple chimeric proteins, wherein the chimeric proteins contain extracellular domains from different antigenic proteins (e.g. H5 in first chimeric protein and a HA protein variant from a seasonal influenza virus in second chimeric protein) are also contemplated within the scope of the invention. These VLPs containing different combinations of chimeric proteins could be used to produce a vaccine directed to several types of influenza virus.

Another embodiment of the invention comprises a method of inducing protective immunity to an infection in a subject, comprising administering to the subject an antigenic formulation or vaccine comprising VLPs, wherein said VLPs comprise at least one influenza membrane protein, but do not contain an influenza matrix (M1) protein. In one embodiment, said VLPs further comprise at least one additional protein from an infectious agent. In another embodiment, said influenza membrane protein is HA. In another embodiment, said HA protein is a seasonal or avian HA. In another embodiment, said VLPs further comprise a NA protein. In another embodiment, said HA and NA are H5N1. In another embodiment, said VLPs do not contain a viral matrix or core protein.

As mentioned above, the VLPs of the invention prevent or reduce at least one symptom of influenza infection in a subject. Symptoms of influenza are well known in the art. They include fever, myalgia, headache, severe malaise, nonproductive cough, sore throat, weight loss and rhinitis. Thus, the method of the invention comprises the prevention or reduction of at least one symptom associated with influenza viral infection. A reduction in a symptom may be determined subjectively or objectively, e.g., self assessment by a subject, by a clinician's assessment or by conducting an appropriate assay or measurement (e.g. body temperature), including, e.g., a quality of life assessment, a slowed progression of an influenza infection or additional symptoms, a reduced severity of a influenza symptoms or a suitable assays (e.g. antibody titer and/or T-cell activation assay). The objective assessment comprises both animal and human assessments.

This invention is further illustrated by the following examples that should not be construed as limiting. The contents of all references, patents and published patent applications cited throughout this application, as well as the Figures, are incorporated herein by reference for all purposes.

EXAMPLES

Example 1

VLP Formation Induced by Expression of Influenza HA and NA Proteins

Influenza A/Sydney/5/97 (H3N2) virus HA, NA M1, M2, and NP genes were expressed in *Spodoptera frugiperda* cells (Sf-9S cell line; ATCC PTA-4047) using the baculovirus bacmid expression system. Infection of permissive Sf-9S insect cells with recombinant baculovirus resulted in co-expression of all five influenza genes or subcombinations thereof in each Sf-9S cell infected with such recombinant baculovirus. The samples, as defined below, are the influenza proteins expressed in a single cell or controls. HPV 16L1, a protein from human papilloma virus, is used as a control.
Samples:
1. HA+NA+NP+M1+M2
2. HA+NA+NP+M1+M2
3. wt baculovirus
4. HA+NA
5. uninfected Sf9 cells
6. HPV 16L1

After growing the infected cells for four days, the cells were pelleted and frozen at −80° C. The cells were thawed at room temperature, resuspended in 4 ml of PBS, pH6.8 and transferred into 560 ml tubes. The cells were sonicated and clarified via centrifugation. Next, Sorvall 12 ml tubes filled with 1 ml of 60% sucrose/PBS, 4 ml of 20% sucrose/PBS pH 6.8 and the clarified cell suspension were placed into a centrifuge tube and centrifuged for 3 hr @28000 rpm. The fractions were taken as depicted in FIG. 1. Approximately 1 ml fractions were collected. Fractions collected at the 20%/60% sucrose interface (fraction 3) typically contain virus-like particles if they are present in the sample. In addition, supernatants of the growth media were saved (after centrifugation) for further analysis.

Figure 2:
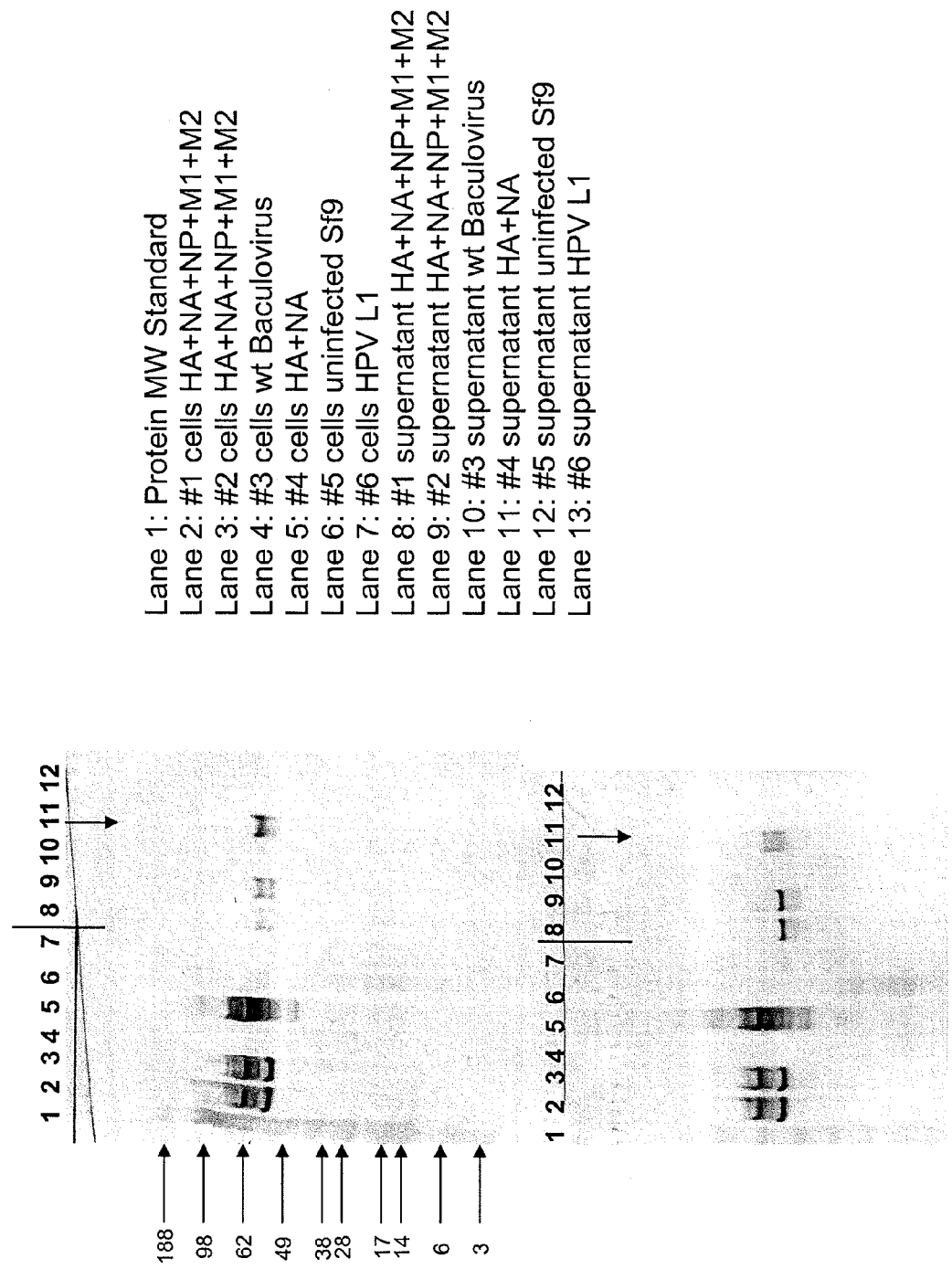
FIG. 2 depicts Western blots of samples from Sf9 cells infected with recombinant baculovirus expressing various combinations of influenza proteins. The samples were purified using a sucrose gradient and fraction 3 (collected as shown in FIG. 1) was loaded onto the gels. The top blot is an analysis of samples taken two days post-infection, while the bottom blot is an analysis of samples taken three days post-infection. Blots were probed with serum against $H3N_2$ influenza virus. Lane 1=molecular weight standard; lanes 2 and 3=cells infected with recombinant baculovirus expressing HA, NA, NP, M1 and M2; lane 4=cells infected with wild-type baculovirus; lane 5=cells infected with recombinant baculovirus expressing HA and NA; lane 6=uninfected Sf9 cells; lane 7=cells infected with recombinant baculovirus expressing HPV 16L1.

Fractions taken from the 20%/60% sucrose interface (fraction 3 in FIG. 1) from the different samples listed above were analyzed by western blot analysis (FIG. 2). Blots of samples taken 2 days (top blot) or 3 days (bottom blot) post-infection were probed with serum against H3N2 influenza virus. Several immunoreactive bands are observed on the blots indicating the presence of influenza viral proteins in virus-like particles. The strongest band represents the immunodominant HA influenza protein. Fractions taken from sample 4 (HA+NA) exhibit immunoreactive bands on these blots (lane 5), indicating VLP formation in cells expressing only HA and NA influenza proteins.

Figure 3:
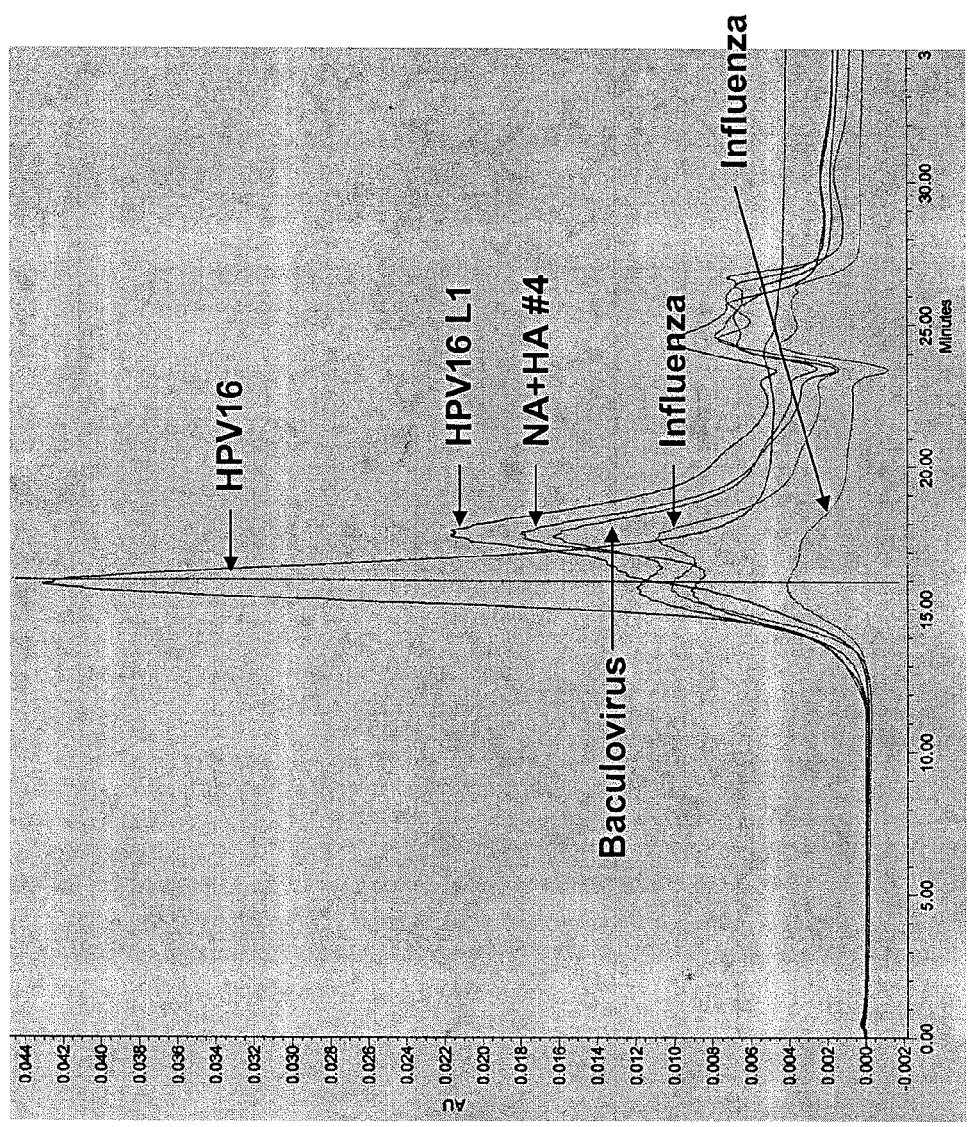
FIG. 3 shows the HPLC chromatographic profile for samples of influenza virions, cells infected with baculovirus expressing HA and NA influenza proteins, and controls.

Samples defined above were also analyzed by high performance liquid chromatography (HPLC). FIG. 3 shows traces obtained from these samples as well as traces from two influenza virus samples. Fractions obtained from cells expressing only influenza HA and NA proteins show a similar chromatographic profile to that of Influenza samples 1 and 2. These data also suggest that VLP formation occurs when the HA and NA proteins are expressed without M1.

Figure 4:
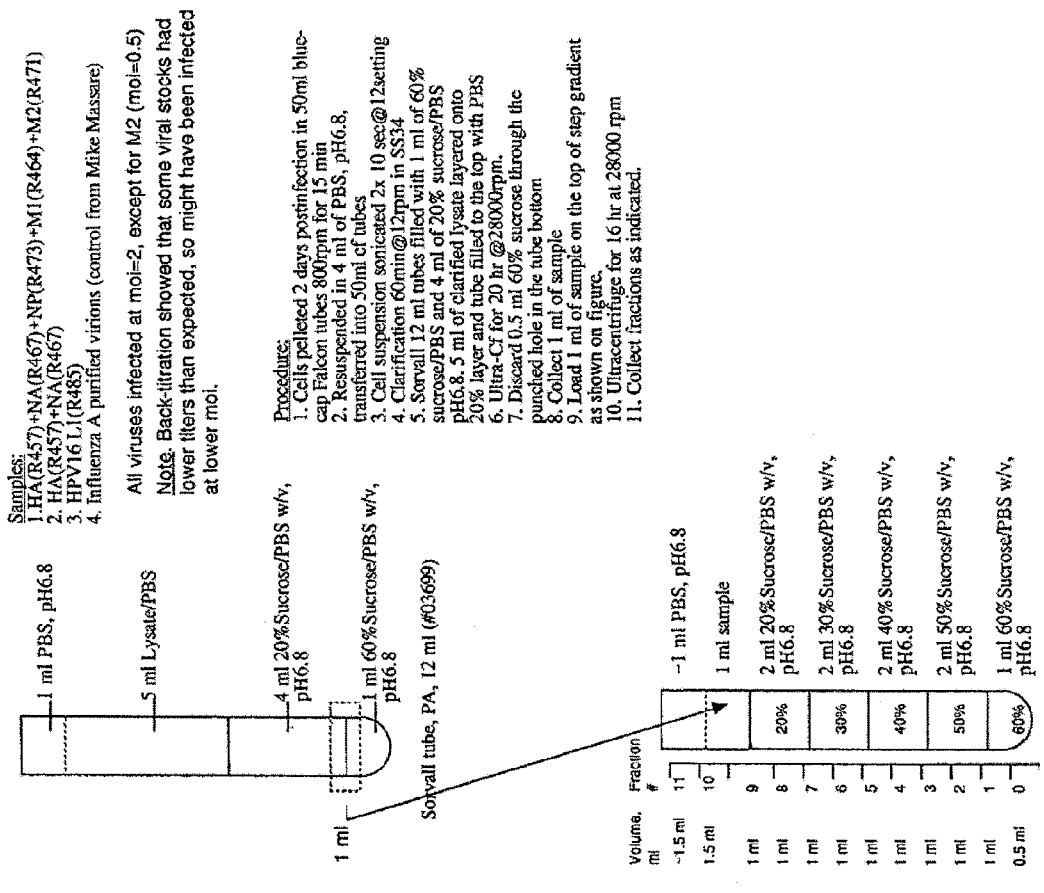
FIG. 4 depicts the procedure for obtaining pure virus-like particles by sucrose gradient ultracentrifugation.

A second experiment similar to the one described above was conducted except that after samples were purified through the sucrose gradient, fractions were further purified through a second sucrose gradient. In this experiment, a 1 ml fraction was collected at the 20%/60% sucrose interface and subjected to a linear sucrose gradient from 20% to 60% (FIG. 4). This gradient was centrifuged for 16 hours @28,000 rpm. The fractions were collected as indicated in the figure. The samples, as defined below, are the influenza proteins expressed in a single cell or controls.
Samples (Cell Lysates):
1. HA+NA+NP+M1+M2
2. HA+NA
3. HPV 16L1
4. Influenza A purified virions
The cell lysates were processed as described above.

Figure 5:
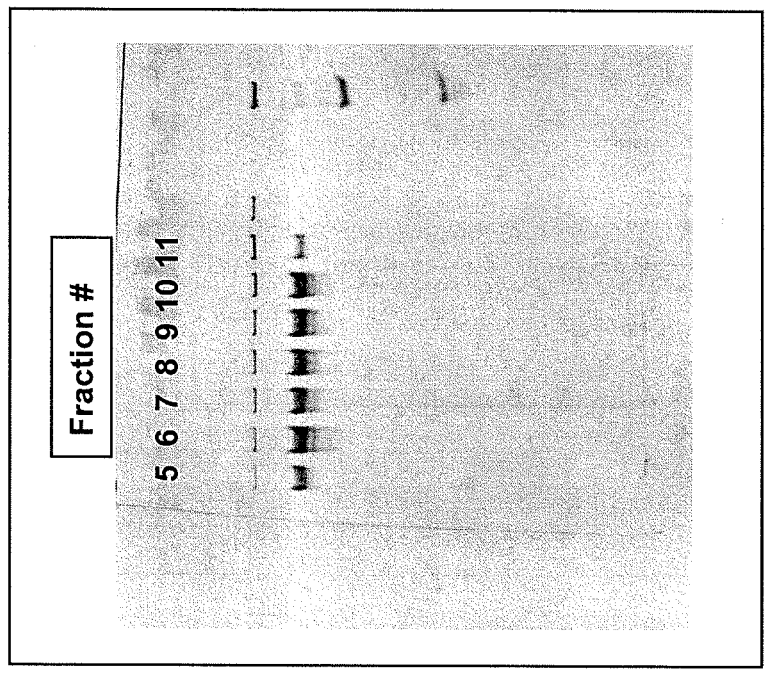
FIG. 5 shows a Western blot of a fractionated sample of cells expressing influenza HA and NA proteins. The blot was probed with serum against $H3N_2$ influenza virus. Lanes 3 through 14 tion provides vaccine compositions that are immunogenic and provide protection. In addition, the term "vaccine" also refers to a suspension or solution of an immunogen (e.g. VLP) that is administered to a vertebrate to produce protective immunity, e.g., immunity that reduces the severity of disease associated with infection or prevents a productive infection.

Cell lysates from sample #2 described above (HA+NA) were processed through the procedure shown in FIG. 4. Fractions collected from the second sucrose gradient were subjected to Western blot analysis (FIG. 5). The blot was probed with serum against H3N2 influenza virus. Lanes 3-14 contain fractions 0-11 collected from the second sucrose gradient. Immunoreactive bands are evident in lanes 5 to 11 suggesting the presence of VLPs in the sample. Note the strongest band (lane 6) correlates to the fraction of the sucrose gradient (30%) where one would expect the majority of VLPs to be located.

Figure 6:
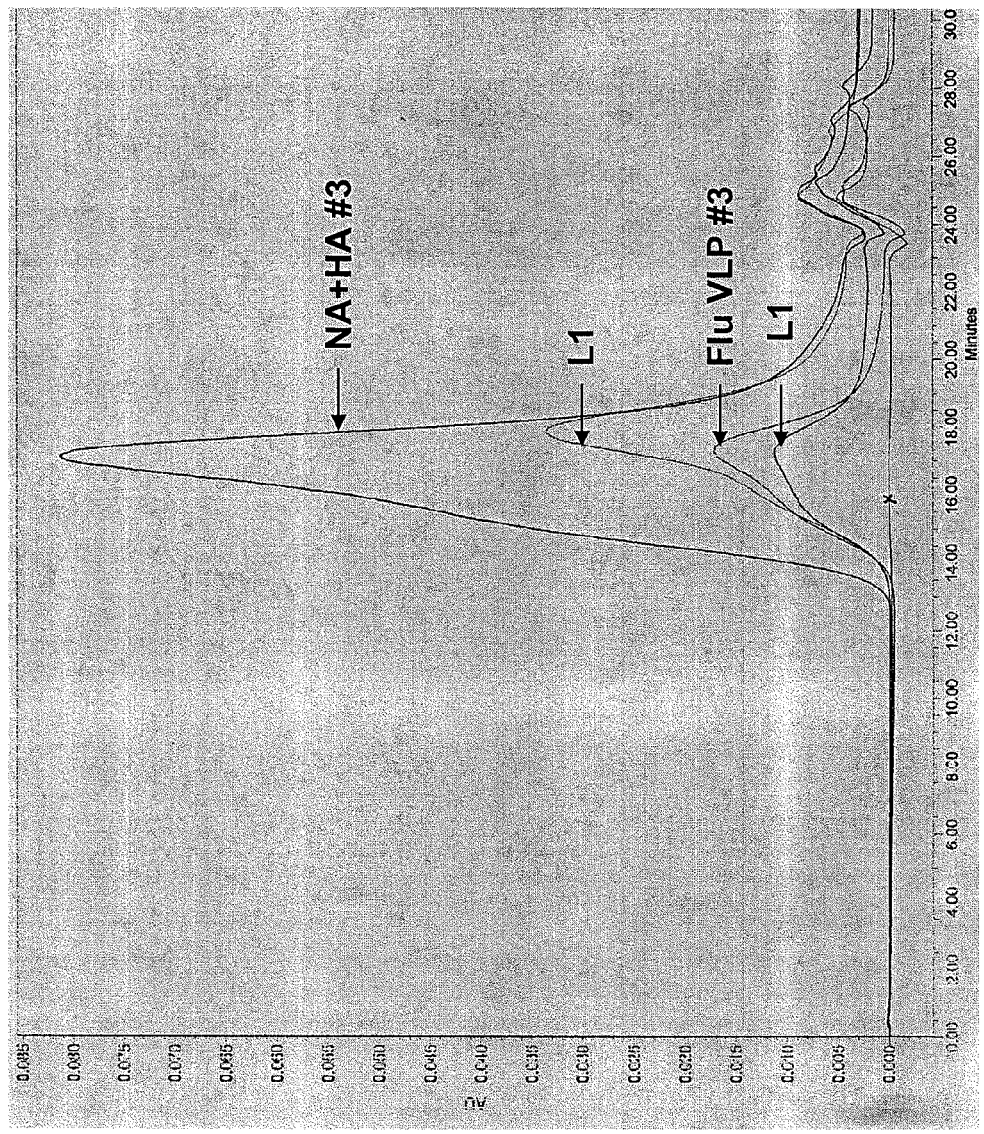

Samples described above (HA+NA, HPV 16L1, and influenza purified virions) were separated by HPLC (FIG. 6). The sample HA+NA#3 has a large peak at about the same size as the control flu VLP#3. These data are indicative of VLP formation in cells expressing HA and NA only.

Example 2

Expression of Single Influenza Membrane Proteins Induces VLP Formation

Figure 7:
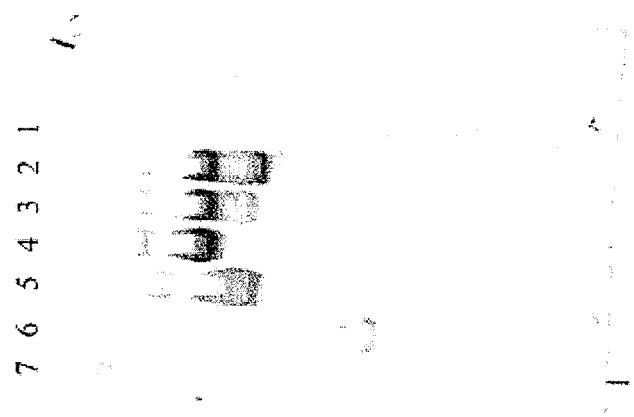

Sf9 cells were infected with recombinant baculovirus expressing various influenza proteins or combinations thereof. Infected cells were incubated in serum-free medium. The media supernatants were pelleted through 20% sucrose cushion. Pellets were resuspended and subjected to western blot analysis. The blot was probed using a polyclonal antibody specific for influenza virus (FIG. 7).

Lanes:
1. Molecular weight standard
2. HA+NA+NP+M1+M2
3. HA+NA+M1+M2
4. HA
5. NA
6. M1
7. M2

Immunoreactive bands are observed in all lanes, but lane 7. These data show that influenza proteins are present in the material, likely VLPs, which could be purified by pelleting through sucrose cushion. Therefore, the supernatant from cells infected with baculovirus expressing either HA protein only, NA protein only or M1 protein only exhibited evidence of VLP formation.

Example 3

Figure 8:
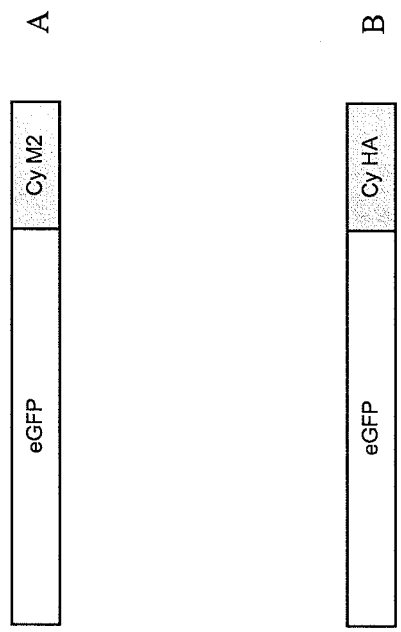
Figure 9:
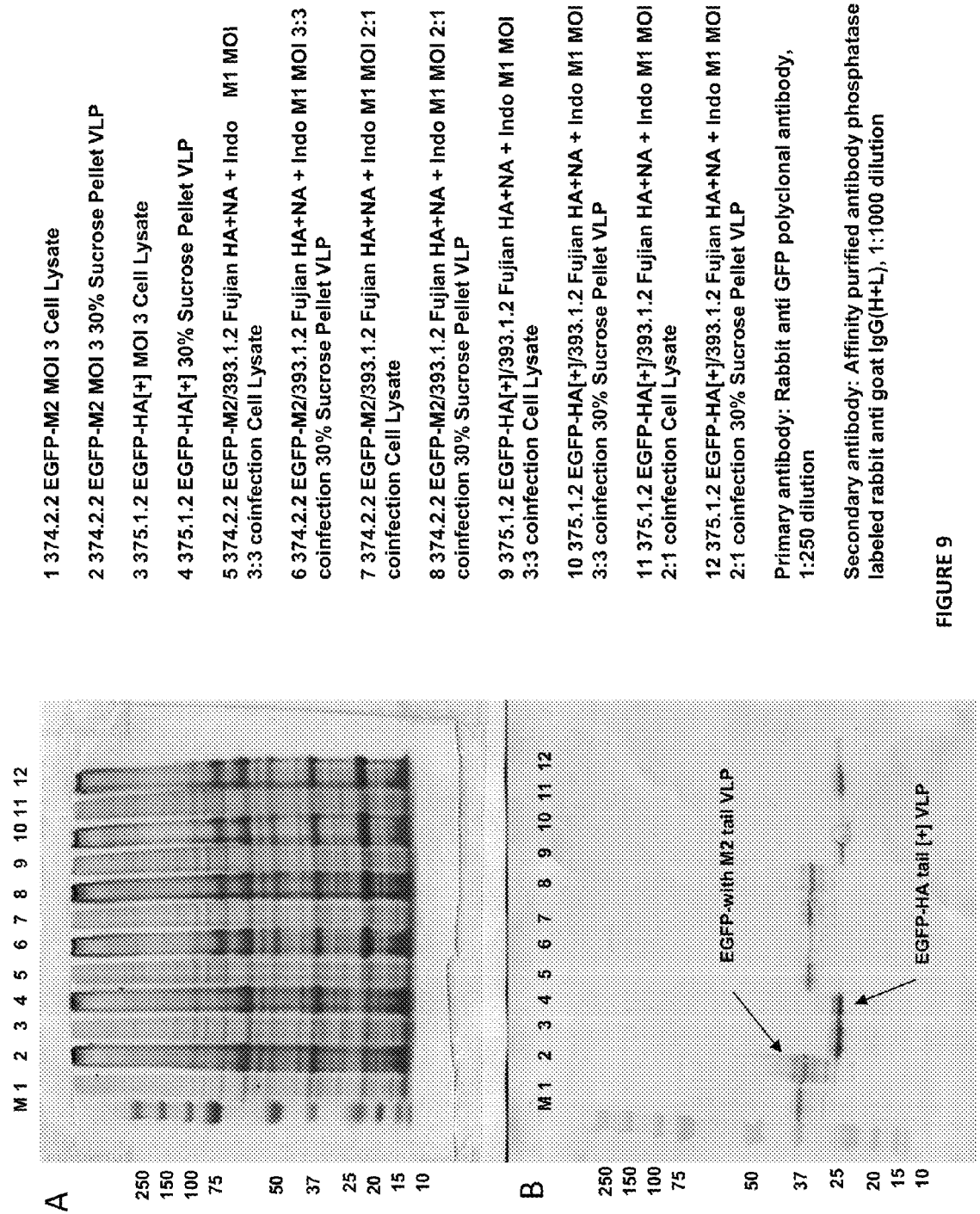

Expression of Chimeric Proteins Derived from Influenza Membrane Proteins Drives VLP Formation Sf9 cells were infected with recombinant baculovirus expressing chimeric proteins. The chimeric proteins contained enhanced green fluorescent protein (eGFP) fused to either the cytoplasmic tail of influenza M2 protein or the cytoplasmic tail of influenza HA protein as illustrated in FIG. 8. Supernatants of the infected cells were purified through a sucrose gradient and subjected to SDS-PAGE and western blot analyses. The resulting coomassie-stained gel is shown in FIG. 9A and the corresponding western blot is shown in FIG. 19B. The blot in FIG. 9B was probed with a polyclonal antibody against GFP. The immunoreactive bands present in lanes 2 and 4 indicate the presence of chimeric proteins (eGFP-M2 cytoplasmic tail and eGFP-HA cytoplasmic tail, respectively) in the supernatant samples purified by sucrose gradient. These data suggest that VLPs are formed in cells expressing the chimeric proteins.

In another experiment, a second type of chimeric protein was constructed, which contained the transmembrane domain of influenza HA protein fused to glycoprotein E (gE) of Varicella Zoster virus (VZV). An example sequence is illustrated below.

```
                                                        SEQ ID NO: 4
VZV gE fused to the transmembrane domain of HA
(underlined)
MGTVNKPVVG VLMGFGIITG TLRITNPVRA SVLRYDDFHT DEDKLDTNSV

YEPYYHSDHA ESSWVNRGES SRKAYDHNSP YIWPRNDYDG FLENAHEHHG

VYNQGRGIDS GERLMQPTQM SAQEDLGDDT GIHVIPTLNG DDRHKIVNVD

QRQYGDVFKG DLNPKPQGQR LIEVSVEENH PFTLRAPIQR IYGVRYTETW

SFLPSLTCTG DAAPAIQHIC LKHTTCFQDV VVDVDCAENT KEDQLAEISY

RFQGKKEADQ PWIVVNTSTL FDELELDPPE IEPGVLKVLR TEKQYLGVYI

WNMRGSDGTS TYATFLVTWK GDEKTRNPTP AVTPQPRGAE FHMWNYHSHV

FSVGDTFSLA MHLQYKIHEA PFDLLLEWLY VPIDPTCQPM RLYSTCLYHP

NAPQCLSHMN SGCTFTSPHL AQRVASTVYQ NCEHADNYTA YCLGISHMEP

SFGLILHDGG TTLKFVDTPE SLSGLYVFVV YFNGHVEAVA YTVVSTVDHF

VNAIEERGFP PTAGQPPATT KPKEITPVNP GTSPLLRQIL SIYSTVASSL

ALAIMMAGLS LWMCSNGSLQ CRICI
```

Sf9 cells were infected with recombinant baculovirus expressing the VZV gE-HA transmembrane chimeric protein. Cell lysates from infected cells were purified through a 20%-60% sucrose density gradient and various fractions collected. Fractions in which VLPs are expected to equilibrate (30% sucrose fraction) were run on an SDS-PAGE gel (FIG. 10A) and subsequently analyzed by western blot. Blots were probed with an antibody against VZV glycoprotein E (FIG. 10B) or an antibody against influenza M1 protein (FIG. 10C). The appearance of bands in lanes 1 and 2 of FIG. 10B indicate the formation of VLPs in cells expressing the chimeric protein containing the transmembrane domain of influenza HA protein fused to gE of VZV.

All patents, publications and patent applications herein are incorporated by reference to the same extent as if each individual patent, publication or cited patent application was specifically and individually indicated to be incorporated by reference.

The foregoing detailed description has been given for clearness of understanding only and no unnecessary limitations should be understood therefrom as modifications will be obvious to those skilled in the art. It is not an admission that any of the information provided herein is prior art or relevant to the presently claimed inventions, or that any publication specifically or implicitly referenced is prior art.

Unless defined otherwise, all technical and scientific terms used herein have the same meaning as commonly understood by one of ordinary skill in the art to which this invention belongs.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

The invention claimed is:

1. A method of making a virus-like particle (VLP) in a cell that comprises at least two influenza membrane proteins, comprising:
   expressing at least a first influenza membrane protein and a second influenza membrane protein in a cell, wherein said first influenza membrane protein is hemagglutinin (HA) and said second influenza membrane protein is neuraminidase (NA) to obtain assembled VLPs; and
   purifying the assembled VLPs, wherein the cell does not express any viral matrix or core protein.

2. The method of claim 1, further comprising expressing at least one additional protein from an infectious agent in said cell, wherein said at least one additional protein from an infectious agent forms part of the VLP.

3. The method of claim 1, wherein said HA is derived from a seasonal influenza virus.

4. The method of claim 3, wherein said seasonal influenza virus is a type A influenza virus.

5. The method of claim 3, wherein said seasonal influenza virus is a type B influenza virus.

6. The method of claim 1, wherein said HA is derived from an avian influenza virus.

7. The method of claim 6, wherein said influenza virus is H5N1.

8. The method of claim 6, wherein said influenza virus is H9N2.

9. The method of claim 1, wherein at least one influenza membrane protein is a chimeric protein comprising the cytoplasmic tail of an influenza membrane protein.

10. The method of claim 9, wherein said cytoplasmic tail of an influenza membrane protein is from HA.

11. The method of claim 1, wherein at least one influenza membrane protein is a chimeric protein comprising the transmembrane domain of an influenza membrane protein.

12. The method of claim 11, wherein said transmembrane domain of an influenza membrane protein is from HA.

13. The method of claim 1, wherein said NA protein is derived from a seasonal influenza virus.

14. The method of claim 13, wherein said seasonal influenza virus is a type A influenza virus.

15. The method of claim 13, wherein said seasonal influenza virus is a type B influenza virus.

16. The method of claim 1, wherein said NA protein is derived from an avian influenza virus.

17. The method of claim 16, wherein said influenza virus is H5N1.

18. The method of claim 16, wherein said influenza virus is H9N2.

19. The method of claim 2, wherein said at least one additional protein from an infectious agent is a chimeric protein.

20. The method of claim 19, wherein said chimeric protein comprises a cytoplasmic and/or transmembrane domain of an orthomyxovirus protein.

* * * * *